US011922374B2

(12) United States Patent
Marinovic

(10) Patent No.: US 11,922,374 B2
(45) Date of Patent: Mar. 5, 2024

(54) SYSTEMS AND METHODS FOR COMMUNICATION SYSTEMS ANALYTICS

(71) Applicant: PwC Product Sales LLC, New York, NY (US)

(72) Inventor: Srdjan Marinovic, Washington, DC (US)

(73) Assignee: PwC Product Sales LLC, New York, NY (US)

( * ) Notice: Subject to any disclaimer, the term of this patent is extended or adjusted under 35 U.S.C. 154(b) by 112 days.

(21) Appl. No.: 17/464,188

(22) Filed: Sep. 1, 2021

(65) Prior Publication Data
US 2022/0067662 A1 Mar. 3, 2022

Related U.S. Application Data

(60) Provisional application No. 63/077,437, filed on Sep. 11, 2020, provisional application No. 63/073,574, filed on Sep. 2, 2020.

(51) Int. Cl.
*G06Q 10/00* (2023.01)
*G06F 16/25* (2019.01)
(Continued)

(52) U.S. Cl.
CPC ......... *G06Q 10/103* (2013.01); *G06F 16/258* (2019.01); *G06Q 10/063118* (2013.01);
(Continued)

(58) Field of Classification Search
CPC .. G06Q 10/101; G06Q 10/103; G06Q 10/106; G06Q 10/063; G06Q 10/063118;
(Continued)

(56) References Cited

U.S. PATENT DOCUMENTS 9,710,767 B1 7/2017 Dietrich et al.
2013/0054708 A1* 2/2013 Bhatt .................. G06Q 10/107
709/206
(Continued)

OTHER PUBLICATIONS

Safapour, E., Kermanshachi, S., Kamalirad, S., & Tran, D. (2019). Identifying effective project-based communication indicators within primary and secondary stakeholders in construction projects. Journal of Legal Affairs and Dispute Resolution in Engineering and Construction, 11(4), 04519028 (10 pp.). (Year: 2019).*

(Continued)

*Primary Examiner* — William S Brockington, III
(74) *Attorney, Agent, or Firm* — Morrison & Foerster LLP

(57) ABSTRACT

Embodiments of this disclosure relate to systems and methods for determining a set of one or more identified characteristics correlated with high performing projects. Methods include receiving communication data from a plurality of servers, the communication data associated with a plurality of conversations involving one or more users. The communication data is converted into a common format and used to generate a graph, the graph based upon characteristics identified in the communication data and users involved with the plurality of conversations. The communication data can be clustered according to the characteristics and the users, thereby generating one or more clusters around at least one of a characteristic and a user. User data and project data can be generated based on the one or more clusters and be used to determine the set of one or more identified characteristics correlated with high performing projects.

22 Claims, 9 Drawing Sheets

(51) Int. Cl.
  *G06Q 10/0631* (2023.01)
  *G06Q 10/0635* (2023.01)
  *G06Q 10/0639* (2023.01)
  *G06Q 10/10* (2023.01)
  *G06Q 10/101* (2023.01)
  *G06Q 10/105* (2023.01)
  *G06Q 50/00* (2012.01)
  *G08B 5/22* (2006.01)
  *G16H 50/30* (2018.01)
  *G16H 50/80* (2018.01)

(52) U.S. Cl.
  CPC ... *G06Q 10/0635* (2013.01); *G06Q 10/06393* (2013.01); *G06Q 10/06398* (2013.01); *G06Q 10/101* (2013.01); *G06Q 10/105* (2013.01); *G06Q 50/01* (2013.01); *G08B 5/22* (2013.01); *G16H 50/30* (2018.01); *G16H 50/80* (2018.01)

(58) Field of Classification Search
  CPC ..... G06Q 10/063112; G06Q 10/06311; G06Q 10/0631; G06Q 10/0635; G06Q 10/0639; G06Q 10/06393; G06Q 10/06398; G06Q 50/01
  See application file for complete search history.

(56) References Cited

U.S. PATENT DOCUMENTS

| | | | |
|---|---|---|---|
| 2015/0170153 A1* | 6/2015 | Sloan | G06Q 30/016 705/304 |
| 2015/0302328 A1* | 10/2015 | Zeng | G06Q 10/06398 705/7.38 |
| 2017/0236081 A1* | 8/2017 | Grady Smith | G06Q 10/0637 705/7.36 |
| 2019/0066029 A1* | 2/2019 | Hancock | G06N 5/04 |
| 2020/0402006 A1* | 12/2020 | Margalit | H04M 1/72403 |

OTHER PUBLICATIONS

International Search Report and Written Opinion dated Dec. 22, 2021, directed to International Application No. PCT/US2021/048640; 12 pages.

* cited by examiner

SYSTEMS AND METHODS FOR COMMUNICATION SYSTEMS ANALYTICS

REFERENCE TO RELATED APPLICATIONS

This application claims the benefit of U.S. Provisional Application No. 63/073,574, filed Sep. 2, 2020, and U.S. Provisional Application No. 63/077,437, filed Sep. 11, 2020, the entire contents of each of which are incorporated herein by reference.

TECHNICAL FIELD

This application relates generally to systems and methods for machine-learning and modeling workflows from disparate data communication systems.

BACKGROUND

Organizations attempt to identify and promote communication patterns associated with successful projects. Organizations, furthermore, work to understand which employees facilitate inter-team communications and drive knowledge sharing. This may be more challenging amongst remote teams (or not proximately located teams) when the usual informal and in-person communications are missing. Informal teams may form without managers' awareness due to the overwhelming amount of communication. These informal teams may, however, be one of the reasons for driving success, in addition to having healthy communication patterns. Generally, when putting teams together project managers will look at the skills that team members have. But in a remote-heavy setting managers ought to make sure that team members are users who, for example, use similar communication tools, have productive communication patterns, or exhibit communication patterns that are beneficial for the project strategies. Such users can be identified by analyzing the user communications through various enterprise communications tools. There are, however, no practical means for efficiently reviewing interactions and communications between enterprise users, across all enterprise communications tools and thus addressing the above-raised issues.

SUMMARY

Described herein are systems and methods for addressing the shortcomings in the state of the art, and providing additional or alternative benefits as well. A server can receive or otherwise extract communication records from across any number of communications tools or services (e.g., Gmail®, Slack®, Skype®, Git®). The server identifies and executes appropriate conversion software modules based on the source communication tools for the communications records. The conversion modules covert the communication records for each of the enterprise users into normalized or otherwise compatible data record format, which can be stored into one or more databases. These converted or integrated data records can include various data fields or labels indicating certain information about the communications, users, past projects, and current projects. The server can execute various processes for generating a graph data structure based upon the converted data records. The server may perform various clustering techniques, such as those previously discussed with respect to hyperclustering, to derive clusters of users who are communicating together and thus forming or operating as teams. The hyperclustering operations (as discussed above with respect to clustering using wireless signals) may be applied to the communications data records to effectively generate, identify, and characterize projects teams and inter-project communication channels.

In an embodiment, a computer-implemented method comprises receiving, by the computer, communication data from a plurality of servers hosting plurality of communication tools, the communication data associated with a plurality of conversations involving one or more users; converting, by the computer, the communication data into a common format; generating, by the computer, a graph based upon the communication data in the common format based upon one or more characteristics identified in the communication data and the one or more users involved with the plurality of conversations; and clustering, by the computer, the communication data in the graph according to the one or more characteristics and the one or more users, thereby generating one or more clusters around at a characteristic.

It is to be understood that both the foregoing general description and the following detailed description are exemplary and explanatory and are intended to provide further explanation of the invention as claimed.

BRIEF DESCRIPTION OF THE DRAWINGS

The accompanying drawings constitute a part of this specification and illustrate embodiments of the subject matter disclosed herein.

DETAILED DESCRIPTION

Figure 1A:
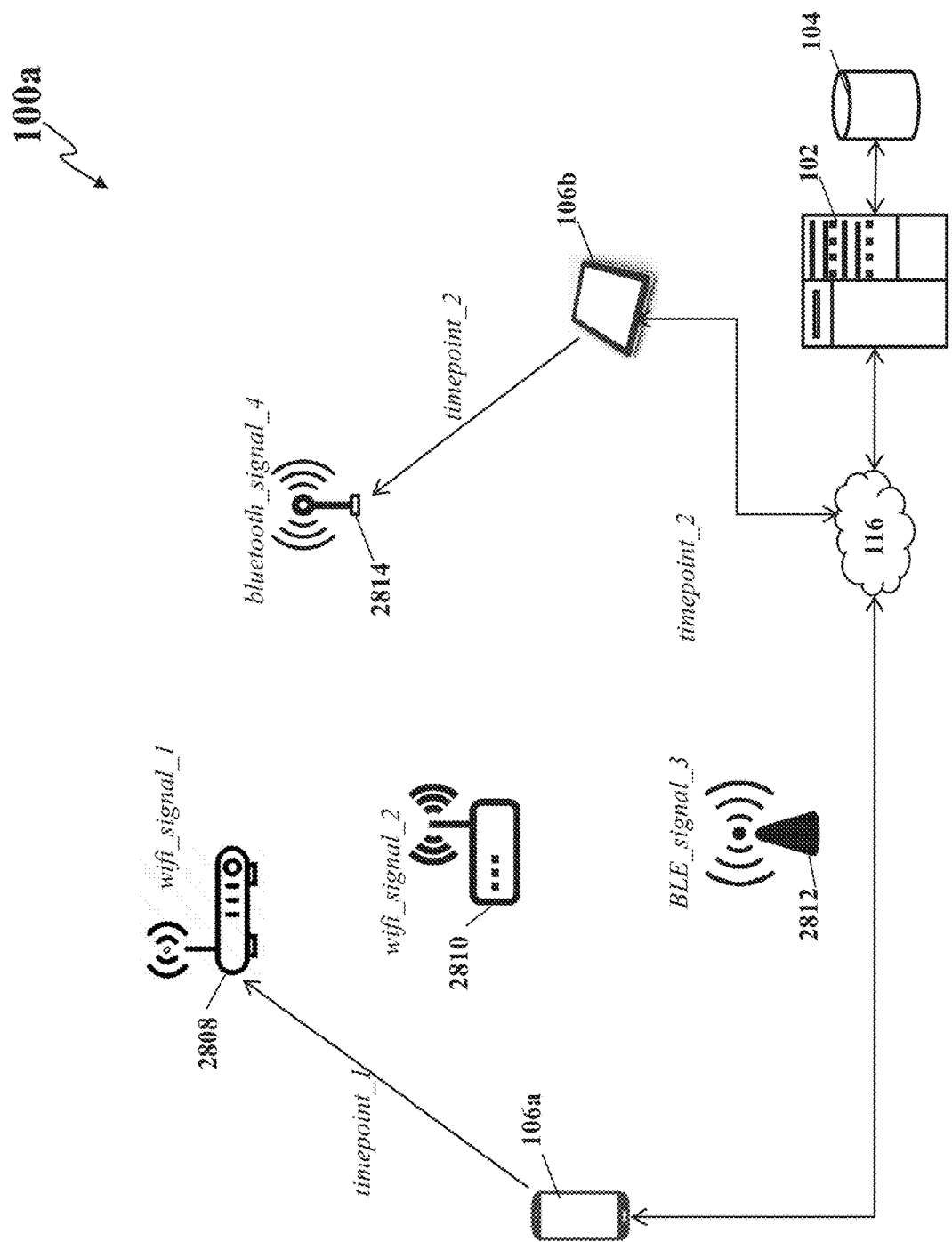
FIGS. 1A-1B illustrate network environments which may be useful for practicing embodiments described herein, according to an embodiment.

Reference will now be made to the illustrative embodiments illustrated in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one ordinarily skilled in the relevant art and having possession of this disclosure, are to be considered within the scope of the subject matter disclosed herein. The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

As would be understood by persons of ordinary skill in the art, any number of the features described in any number of the embodiments below may be combined into a single embodiment, and the description of any features in separate embodiments is not intended to be limiting.

In general, as described in the below passages, an analytic server may monitor wireless signals detected by a plurality of electronic devices and, in some embodiments, generate data structures representing hyperclusters (also sometimes referred to as, "signal clusters" or "proximal groupings" of devices) by analyzing the wireless signals and detected observation received in the wireless signals. The analytic server and system database may receive and store observed data, which includes the interactions of an electronic device with other devices in an environment and/or one or more hyperclusters comprising other devices. When the analytic server receives a request from an enterprise server (e.g., human resources administrator server) or client computing devices (e.g., administrator computer) to trace the interactions of a particular target device, the analytic server may identify other electronic devices in the ecosystem that have interacted with the target device, based on the observation data for the target device and other electronic devices. More specifically, the analytic server may receive the observation data from the observer devices; each of the observer devices receive and report (or observe) observation data based on the wireless signals broadcasted by the target device and by the target device itself.

The analytic server may determine a risk score for infection based on, for example, values in the observation data, a signal context (e.g., associated hypercluster, label data), identified patterns of behavior, weighted values for comparatively busy or empty spaces, and a geolocation (e.g., office location) of the target device as indicated in the observations from the observer devices. In addition, the analytic server may perform a resolution of the wireless signals within the hypercluster to assign semantic meanings to the wireless signals. The semantic meaning may provide useful information on the location or environment that the target device was at some time point located in, such as location, business, and any other knowledge, which may weight or adjust a risk score in order refine the quality, accuracy, and precision of the risk score.

An administrative user of an enterprise network may enter a tracing request into a client computing device to tracing the interactions between devices of the system and the target device. The tracing request may trigger a client computing device of the enterprise network to query an enterprise administration database that stores correspondences between observer device identifiers and user employee identifiers or information. The tracing request may indicate an employee identifier and a given time frame; the query returns the corresponding observer device identifier. This observer identifier is for the target observer device, and is submitted as a query to the analytics server. The analytics server identifies in an analytics database, each of the observer identifiers that were in contact with the target observer device and generates risk scores for each of the observer devices and/or the target observer device. The results of these calculations may be presented to the administrator via a GUI on the client computing device. The analytics server does not have access to the administrator database, so the analytics server is unable to access and return employee identifiers. Rather, the analytics server returns the outputted analytics data and observer identifiers.

The client computing device or server may query the administrator database to identify and resolve which user employees correspond to the observer identifiers mentioned in the output from the analytics data.

I. Tracing Devices Using Proximal Groups of Devices

Embodiments herein describe systems and methods for locating and/or tracing interactions between devices using proximal groups of devices. FIG. 1A illustrates a network environment 100 which may be useful for practicing embodiments described herein, according to an embodiment. The network environment 100 may include an analytic server 102 and a database 104 coupled to the analytic server 102. The network environment 100 may include observer devices 106a, 106b (collectively referred to as, "observer devices 106") that are interconnected with analytic server 102 via a network 116. The network environment 100 may include a Wi-Fi router 108, a Wi-Fi router 110, a BLE transmitter 112, and/or a Bluetooth transmitter 114. Although FIG. 1A shows only a select number of computing devices (e.g., observer devices, Wi-Fi routers, BLE transmitters, Bluetooth transmitters, etc.), the network environment 100 may include any number of components (in any combination) that are interconnected in any arrangement to facilitate the exchange of data between the computing devices.

The analytic server 102 may function as an interface for an administrator to set configuration settings or provide operational instructions to various components of the network environment 100. The analytic server 102 may be any computing device comprising a communications component capable of wired or wireless communication with other components of the network environment 100, and a microprocessor configured to transmit and receive certain types of data from the components of the network environment 100.

Non-limiting examples of the analytic server 102 may include a server (e.g., an application server, a catalog server, a communications server, a computing server, a database server, a file server, a game server, a mail server, a media server, a proxy server, a virtual server, a web server, etc.) a personal computer, a laptop computer, a desktop computer, a mobile computer, a tablet computer, a smart phone, a digital video recorder, a set-top box for a television, a video game console, a digital wallet (sometimes referred to as an "e-Wallet"), or any other type and form of computing device or combinations of devices. In some embodiments, the type of analytic server 102 may be categorized as a mobile device, a desktop device, a device intended to remain stationary, a device adapted to primarily access a network via a local area network (e.g., network 116), or another category of electronic devices such as a media consumption device. The analytic server 102 may include a user application (e.g., a web browser, an email application, an FTP application, etc.) to facilitate the sending and receiving of data over network 116.

For ease of explanation, FIG. 1A shows a single computer device functioning as the analytic server 102. However, it should be appreciated that some embodiments may comprise any number of computing devices functioning as the analytic server 102 and capable of performing the various tasks described herein The analytic server 102 may receive information on wireless signals (sometimes referred to as, "signals") detected by one or more observer devices 106 through a network 116 to generate one or more hyperclusters (sometimes referred to as, "proximal groupings of electronic devices"). The analytic server 102 may receive identification information about wireless signals (sometimes referred to as, "signals") detected by one or more of the observer devices 106a, 106b. In response to receiving the identification information, the analytic server 102 may generate one or more hyperclusters using the identification information, and/or store the identification information and hyperclusters in the database 104 for further processing.

The analytic server 102 may explain the relationships in the physical world by measuring relationships between signals and devices. By approximating the world via temporal relationships between signals, the analytic server 102 may build a dataset to compute temporal persistence between devices. This dataset may be referred to as a signal graph (sometimes referred to as, "SignalGraph"). The signal graph is temporal graph model that may connect signals and observers into a network. The signal graph may comprise signals and observers (e.g., observer devices that observe the signals) at different time points.

The signal graph may provide information about relationships in the physical world. For example, the analytic server 102 may generate a set of hyperclusters (or signal clusters or proximal grouping of electronic devices) based on the spatial proximity and temporal persistence of the wireless signals. A hypercluster may be a set of signals that have been observed together within a number of observations. A given hypercluster may represent a set of devices that remain in physical proximity over time. In other words, a hypercluster is a static relationship between signals, as the proximity persists across time and observations.

The analytic server 102 may be directly or indirectly connected to observer devices 106a, 106b and database 104. Accordingly, the analytic server 102 may be capable of wired or wireless communication through a variety of communication channels with the observer devices 106a, 106b and the database 104 over a network 116. During the wired or wireless communication between the analytic server 102, the observer devices 106a, 106b, and the database 104, each of these devices may be capable to transmitting and receiving data from each other. In some embodiments, each of these devices may normalize and format the data in accordance to pre-stored instructions prior to transmitting the data to other devices. In some embodiments, each of these devices may store a local copy of the data in their memory prior to transmitting original copy of the data to other devices.

Examples of a network 116 may include, but are not limited to, private or public LAN, WLAN, MAN, WAN, and Internet. The network 116 may include both wired and wireless communications channels according to one or more standards and/or via one or more transport mediums. The communication over the network 116 between the components of the network environment 100 may be performed in accordance with various communication protocols such as Transmission Control Protocol and Internet Protocol (TCP/IP), User Datagram Protocol (UDP), and IEEE communication protocols. In one example, the network may include wireless communications according to Bluetooth specification sets, or another standard or proprietary wireless communication protocol. In another example, the network may also include communications over a cellular network, including, e.g., a GSM (Global System for Mobile Communications), CDMA (Code Division Multiple Access), and EDGE (Enhanced Data for Global Evolution) network.

Observer devices 106a, 106b may be any computing and/or telecommunications devices comprising a processor and capable of performing various tasks and processes described herein. Non-limiting examples of the observer devices may include a telephone 106a (e.g., smartphone), a user computer 106b (e.g., desktop, laptop, server, tablet), or any other telecommunications or computing device capable of performing the various tasks and processes described herein. For ease of explanation, FIG. 1A shows two devices functioning as the observer devices 106a, 106b. However, it should be appreciated that some embodiments may comprise any number of observer devices capable of performing the various tasks described herein.

In some embodiments, observer devices 106a, 106b may be computing devices that function as sensor devices, and are directly or indirectly associated with an analytic server 102 and/or a database 104. The sensor devices may be capable of observing signals in their zone of operation emitted by various devices such as IoT devices. The sensor device may further include a sensor processor configured to process the observed signals and extract identification information from the observed signals. Non-limiting examples of the sensor technologies for the sensor devices may include resonant LC sensors, capacitive sensors, and inductive sensors. Based upon the particular type of the sensor waves used and the particular protocols associated with the sensor waves, the sensor devices may observe signals and then generate sensor data, which may include information associated with the observed signals. The sensor processor may receive, interpret, and process sensor data, which the sensor may then provide to a processor of the analytic server 102 and/or the database 104.

Each observer device may include identification information. The identification information may include a name of the observer device, a type of the observer device, a model number of the observer device, a location information of the observer device, and an ID of the observer device where the ID may be pseudo-random identifier such as a hash value. In some cases, each observer device may have multiple IDs and the IDs may change at any time. All past and current identification information of each of the observer device may be stored in a database 104. For example, a given observer device may have an old ID and a new ID, and in such as case, both the old and new IDs may be stored in the database 104. The analytic server 102 may have access to the identification information of each observer device stored in a database 104. The analytic server 102 may generate a query and/or a request and transmit the query and/or the request at any time to the database 104 to receive identification information of any observer device. In some cases, the analytic server 102 on receiving signal data from the observer device may query the database 104 to receive additional identification information regarding the observer device from which it received the signal data.

The analytic server 102 may set configuration settings or provide operational instructions to observer devices 106a, 106b to make observations of signals transmitted by various devices such as Internet of Things (IoT) devices and then provide analytics and data about signal observation application activity back to the analytic server 102. In some embodiments, the analytic server 102 may generate and transmit the operational instructions to the observer devices 106a, 106b at any point of time in order to enable the observer devices 106a, 106b to make the observations of the signals transmitted by various devices such as IoT devices, and then provide analytics and data about signal observation application activity back to the analytic server 102. In some embodiments, the analytic server 102 may generate and transmit the operational instructions to the observer devices 106a, 106b at any point of time in order to disable the observer devices 106 from making any observations of the signals transmitted by various devices such as IoT devices, and then notify the successful disablement of the observer devices 106a, 106b back to the analytic server 102. In some embodiments, the analytic server 102 may also transmit a weblink of configuration settings to the observer devices 106a, 106b, and the observer devices 106a, 106b may use the weblink for installation of the configuration settings in their hardware and/or software. The configuration settings may enable or disable the observer devices 106a, 106b to make the observations of the signals transmitted by various devices such as IoT devices, and then provide analytics and data about signal observation application activity back to the analytic server 102. In some cases, the configuration settings may enable the observer devices 106a, 106b to make the observations of the signals transmitted by various devices such as IoT devices for a limited period of time (such as 2 hours a day) in the day, and the same configuration settings may also disable the observer devices 106a, 106b from making any observations of the signals during the rest of the day. In some cases, the configuration settings may disable the observer devices 106a, 106b from making any observations of the signals when their battery charge is below a predetermined threshold. For this purpose, the configuration settings may allow the analytic server 102 to constantly monitor battery charge of the observer devices 106a, 106b and when the battery charge is below a predetermined threshold, and then the analytic server 102 may disable the observer devices 106a, 106b from making any observations of the signals. In some cases, the configuration settings may disable some applications of the observer devices 106a, 106b when their battery charge is below a predetermined threshold to allow the observer devices 106a, 106b from making observations of the signals. In some embodiments, the configuration settings may instruct the observer devices 106a, 106b to send to the analytic server 102 signals associated with specific types of devices or entities such as signals associated with businesses or other enterprises. The configuration settings may instruct the observer devices 106a, 106b not to send signals associated with individuals' personal devices (e.g., fitness trackers) to the analytic server 102.

The analytic server 102 may receive data including wireless signals detected by observer devices 106a, 106b. In some embodiments, the observer devices 106a, 106b may transmit the data including observed signals to the analytic server 102 as soon as the analytic server 102 detects any signals. In some embodiments, the observer devices 106a, 106b may transmit the observed signals to the analytic server 102 after a predetermined period of time. For example, the observer devices 106a, 106b may be programmed to periodically (e.g., daily) transmit data including all observed signals to the analytic server 102. In some embodiments, the analytic server 102 may fetch data including the observed signals data from the observer devices 106a, 106b periodically (e.g., daily). In some embodiments, the analytic server 102 may fetch data including the observed signals data from the observer devices 106a, 106b based on a triggering condition (e.g., time-based periodic updates, real-time updates). The data may include, but may not be limited to, all observed wireless signals, a time point at which each wireless signals was observed, approximate latitude coordinates of where event of observation is recorded, approximate longitude coordinates of where event of observation is recorded, among other data and identification information.

The analytic server 102 may store into the database 104 all the observation data, such as observed wireless signals, a signal strength value (e.g., RSSI), a time point at which each wireless signals was observed, and, in some implementations, approximate latitude coordinates of where event of observation is recorded, and approximate longitude coordinates of where event of observation is recorded in a database 104 for further processing. In some embodiments, the analytic server 102 may store all the data in the database 104 in a format in which all the data was received by the analytic server 102. In some embodiments, the analytic server 102 may first normalize and format all the data, and then store the normalized and formatted version of the data in the database 104. The analytic server 102 may use any suitable normalization and formatting technique to normalize and format all the data depending on content, received format, structure, and size of the data. Upon normalization and formatting of the data, the analytic server 102 may execute algorithms such as clustering algorithms to generate one or more hyperclusters of the signal datasets. Each hypercluster may represent a set of signals that have been observed together by the observer devices 106a, 106b within a number of observations made by the observer devices 106a, 106b. In some cases, for every two observations in the hypercluster, there may exist at least two overlapping observations that contain said two observations.

As illustrated in FIG. 1A, a first observer device 106a (e.g., a smartphone, a tablet, or other device, etc.) may detect, at timepoint_1, wifi_signal_1 generated by a first Wi-Fi router 108 and wifi_signal_2 generated by a second Wi-Fi router 110. A second observer device 106b (e.g., a smartphone, a tablet, or other device, etc.) may detect, at timepoint_2, wifi_signal_1 generated by the first Wi-Fi router 108, bluetooth_signal_4 generated by Bluetooth transmitter 114, BLE_signal_3 generated by a Bluetooth low energy (BLE) transmitter 112. Furthermore, the first observer device 106a may detect, at timepoint_3, the BLE_signal_3 generated by the BLE transmitter 112. Each of the aforementioned signals may include a tuple of (name, MAC_address, type). Two signals may be equivalent of all three elements are equivalent.

Each observer device 106a, 106b may transmit through the network 116 information of the detected signals to the analytic server 102 for storage in the database 104 and for further analysis. Based on the temporal persistence and spatial proximity of the signals observed by the observer devices 106a, 106b and received by the analytic server 102, the analytic server 102 may define one or more hyperclusters (or proximal groupings of electronic devices) associated with the location where the signals are received from.

A data model employed by the analytic server 102 to identify the hyperclusters (e.g., proximal groupings of electronic devices) may include a set of signals S observed by a population of observer mobile devices U. In the illustrative network environment 100a, S={wifi_signal_1, wifi_signal_2, BLE_signal_3, bluetooth_signal_4} and U={106a, 106b}. As described above, each of the signals in the set of signals S may include a tuple of (name, MAC_address, type). The analytic server 102 may identify each observer device 106 with a respective mobile advertising identifier or any other identifier assigned to or associated with the app or observer device 106 (e.g., observation identifier), abbreviated as adid or obsvID. The analytic server 102 may associate each adid of the observer devices 106a, 106b with a matrix of signals and time points. More specifically, the analytic server 102 may construct a sparse Boolean matrix to denote which signals an observer adid observed in a given time window. In other words, the Boolean matrix for the observer device 106a, 106b may indicate a presence of (indicated by entry 1) or absence of (indicated by entry 0)

one or more signals, as detected by the observer device 106a, 106b for a particular time period. The analytic server 102 may, however, discard signals at stale time points as reported by the observer devices 106a, 106b even though the stale time points may not indicate a nefarious behavior. For example, if an observer device 106a, 106b has a single observation that stretches credulity (threshold set at more than five days lag), the analytic server 102 may simply remove the observation. In some embodiments, the observer devices 106a, 106b may also transmit the respective latitude longitude coordinates of the observer devices 106a, 106b. In some instances, the observer devices 106a, 106b may observe the wireless location signals from coinciding locations. For example, the latitude longitude coordinates of the observer devices 106a, 106b may be the same.

Figure 1B:
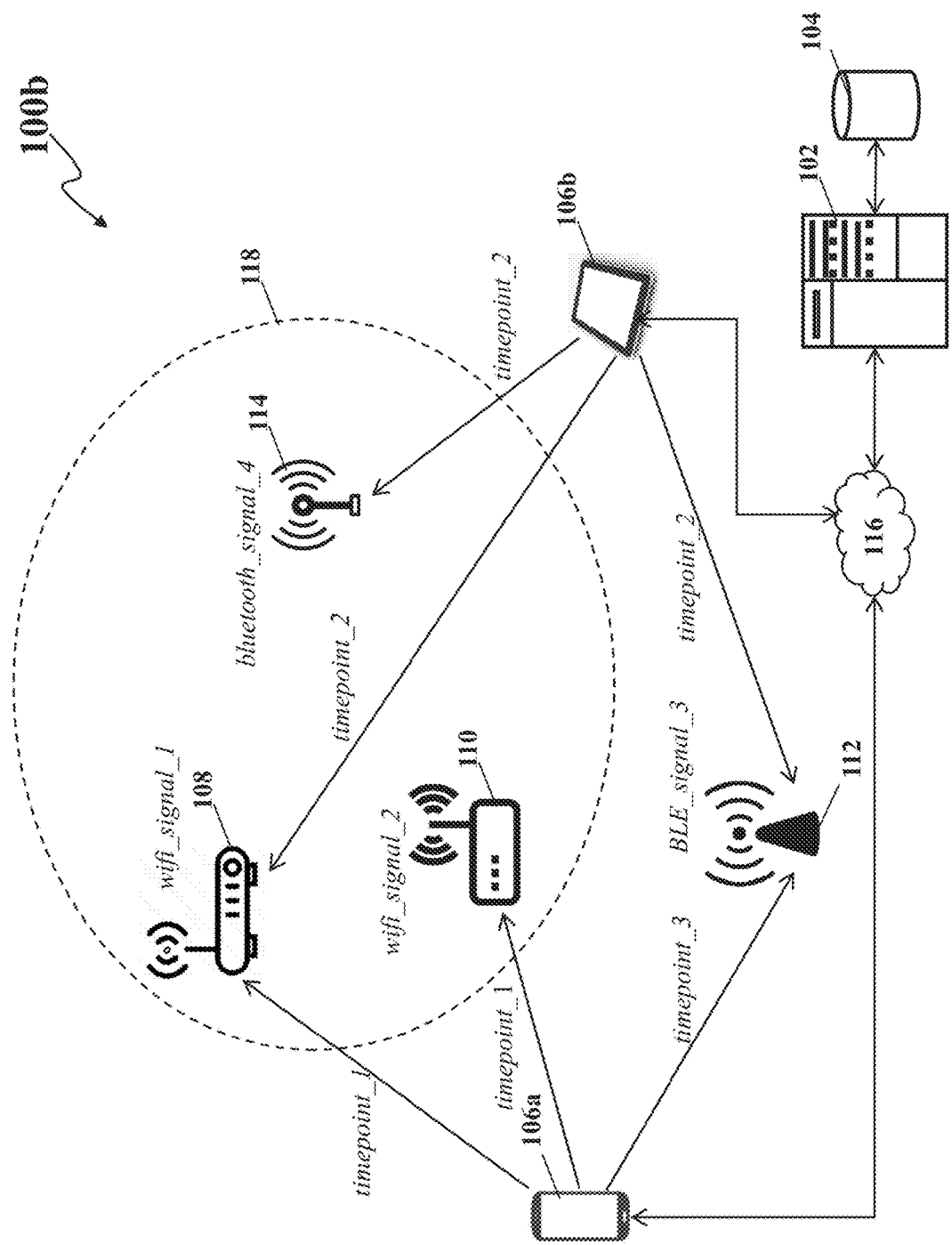

Based on the analysis of the matrices associated with the observer devices 106, the analytic server 102 may generate one or more hyperclusters based on the temporal persistence and spatial proximity of the received signals. For example, FIG. 1B illustrates a network environment 100b which may be useful for practicing embodiments described herein, according to an embodiment. That is, a network environment 100b may include a hypercluster 118 that is generated by the analytic server 102 based on the wireless signals detected by the observer devices 106. In this illustration, the hypercluster 118 may contain three wireless signals: wifi_signal_1, wifi_signal_2, bluetooth_signal_4. The analytic server 102 may determine the spatial proximity of wifi_signal_1, wifi_signal_2, bluetooth_signal_4 based on the fact that the these signals were detected simultaneously or near-simultaneously by the observer devices 106a, 106b. The analytic server 102 may determine the temporal persistence of wifi_signal_1, wifi_signal_2, bluetooth_signal_4 based on the fact that the two observer devices 106a, 106b observed these signals at two time points: the first observer device 106a observed these signals at timepoint_1 and the second observer device 106b observed these signals at timepoint_2. However, the analytic server 102 may determine that BLE_signal_3, even though having spatial proximity with wifi_signal_1, wifi_signal_2, bluetooth_signal_4 may not have the requisite temporal persistence. For example, the first observer 106a did not detect BLE_signal_3 at timepoint_1.

The observer devices 106a, 106b may be directly or indirectly connected to the analytic server 102 and a database 104. Accordingly, the observer devices 106a, 106b may be capable of wired or wireless communication through a variety of communication channels with the analytic server 102 and the database 104 over a network 116. During the wired or wireless communication between the observer devices 106a, 106b, the analytic server 102, and the database 104, each of these devices may be capable to transmitting and receiving data from each other. In some embodiments, the observer devices 106 may normalize and format the data in accordance to pre-stored instructions prior to transmitting the data to the analytic server 102 and/or the database 104. In some embodiments, the observer devices 106a, 106b may store a local copy of the data in their memory prior to transmitting original copy of the data to the analytic server 102 and/or the database 104.

The observer device 106a, 106b may be configured to observe an event. The event may contain all signals that the observer device 106a, 106b scanned around its zone of operation at a given time point. Accordingly, the event may include observed signal data, and in some cases, the event may also include approximate or correct values of latitude coordinates of where the event is recorded by the observer device 106a, 106b at a given time point. In some cases, the event may further include approximate or correct values of longitude coordinates of where the event is recorded by the observer device 106a, 106b at a given time point.

The event is caused when observer device 106a, 106b observes signals from various devices such as IoT devices. The signals may be an electromagnetic signal emitted by the IoT devices. It is to be noted that the signal may be any type of signal emitted by the IoT devices without moving out the scope of the disclosed embodiments. The signals observed by the observer device 106a, 106b may represent discrete values about the signals. In some embodiments, the discrete values of the signals may be characterized by a type of signal. The type of signal may include, but may not be limited to, a Bluetooth® signal, wireless fidelity (Wi-Fi) signal, or Bluetooth Low Energy (BLE) signals. In some embodiments, the discrete values of the signals may further be characterized by a name of signal. The name of the signal may be a SSID (service set identifier) that identifies an IoT device. The SSID may be a unique ID that consists of 32 characters and is used for naming wireless networks. In some embodiments, the discrete values of the signals may further be characterized by an address of the IoT device through which the device communicates the signal. Each IoT device may emit multiple signals.

Network components may effectuate wired and/or wireless signal communications to and from various devices. The network components may include transmitters, a first Wi-Fi router 108, a second Wi-Fi router 110, and a Bluetooth low energy (BLE) transmitter 112. These network components may be an embedded component of an electronic device; and, in some cases, the network component may be attached to the electronic device through any wired or wireless communications medium. The network components such as the first Wi-Fi router 108, the second Wi-Fi router 110, and the Bluetooth low energy (BLE) transmitter 112 may include electromechanical components (e.g., processor, antenna) that allow the network components to communicate various types of signal data with one or more electronic devices. In some implementations, these signals may represent a distinct channel for hosting communications. The data may be communicated using signals, based on predetermined wired or wireless protocols and associated hardware and software technology. The network components may operate based on any number of communication protocols, such as Bluetooth®, Wireless Fidelity (Wi-Fi), and others.

Databases 104 may be directly or indirectly connected to observer devices 106a, 106b and an analytic server 102. Accordingly, the database 104 may be capable of wired or wireless communication through a variety of communication channels with the observer devices 106a, 106b and the analytic server 102 over a network 116. During the wired or wireless communication between the analytic server 102, the observer devices 106a, 106b, and the database 104, the database 104 is capable of receiving data from the analytic server 102 and the observer devices 106. The data may include, but may not be limited to, all observed wireless signals, a time point at which each wireless signals was observed by the observer devices 106a, 106b, approximate latitude coordinates of where event of observation is recorded by the observer devices 106a, 106b, approximate longitude coordinates of where event of observation is recorded by the observer devices 106a, 106b, among other data and identification information. For ease of explanation, FIG. 1A shows a single database 104. However, it should be appreciated that some embodiments may comprise any number of databases capable of performing the various tasks described herein.

The database 104 may have a logical construct of data files that are stored in non-transitory machine-readable storage media, such as a hard disk or memory, controlled by software modules of a database program (for example, SQL), and a related database management system (DBMS) that executes the code modules (for example, SQL scripts) for various data queries and other management functions generated by the analytic server 102 and the observer devices 106a, 106b. In some embodiments, a memory of the databases 104 may be a non-volatile storage device. The memory may be implemented with a magnetic disk drive, an optical disk drive, a solid-state device, or an attachment to a network storage. The memory may include one or more memory devices to facilitate storage and manipulation of program code, set of instructions, tasks, data, PDKs, and the like. Non-limiting examples of memory implementations may include, but are not limited to, a random access memory (RAM), a read only memory (ROM), a hard disk drive (HDD), a secure digital (SD) card, a magneto-resistive read/write memory, an optical read/write memory, a cache memory, or a magnetic read/write memory. In some embodiments, a memory of the databases 104 may be a temporary memory, meaning that a primary purpose of the memory is not long-term storage. Examples of the volatile memories may include dynamic random access memories (DRAM), static random access memories (SRAM), and other forms of volatile memories known in the art. In some embodiments, the memory may be configured to store larger amounts of information than volatile memory. The memory may further be configured for long-term storage of information. In some examples, the memory may include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

In operation the analytic server 102 may utilize the hypercluster 118 (or proximal grouping of wireless devices 108, 110, 114) to generate a semantic to one or more wireless signals. For example, if the hypercluster 118 is observed by multiple devices throughout the day and not observed by any device during the night, the analytic server 102 may determine that the hypercluster 108 may be within an office and the devices 108, 110, 114 may be installed in an office. If the hypercluster 118 is persistently observed by a few devices, the analytic server 102 may determine that the hypercluster 108 may be within a home and the devices 108, 110, 114 may be installed in a home. The analytic server 102 may also distinguish between enterprise and business signals (e.g., router associated with a company or a chain location) and personal signals (e.g., a BLE signal emitted by a person's fitness tracker). In particular, the analytic server 102 may include a trained classifier to classify whether an observed signal is associated with a particular location (e.g., cafeteria, conference room, gym) or a person. Such classification may allow the analytic server 102 to perform operations in a manner that respects individuals' expectation of privacy and complies with privacy rules in different jurisdictions.

Figure 1C:
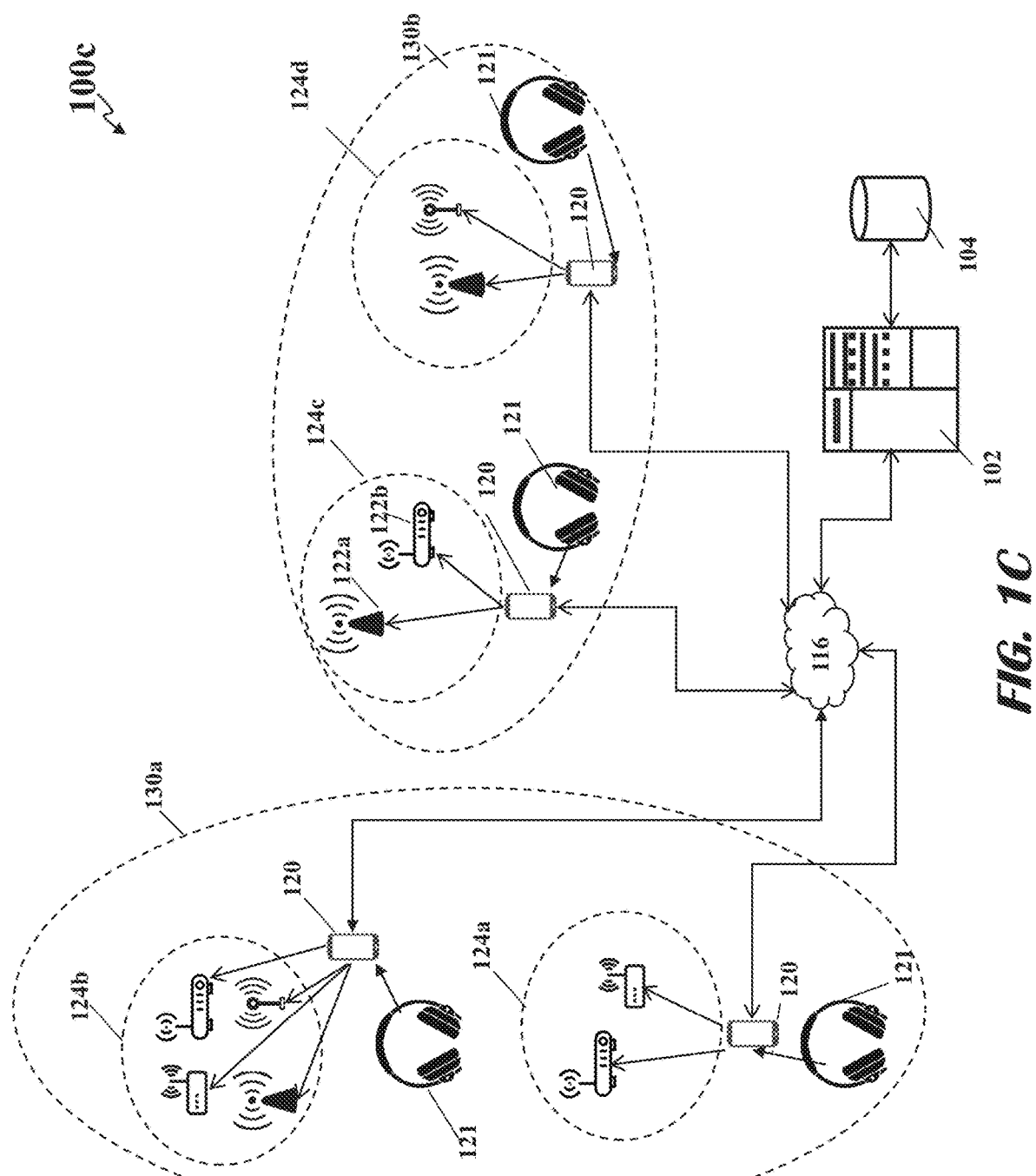
FIG. 1C illustrates a network environment for locating and/or tracing electronic devices, according to an embodiment.

FIG. 1C illustrates a network environment 100c for locating and/or tracing interactions between electronic devices, according to an embodiment. The analytic server 102 may receive an indication from another server (not shown) that a mobile app has been installed on the observer electronic device 120. In response, the analytic server 102 may communicate with the observer electronic device 120 or one or more apps installed therein to trace the interactions of the observer electronic device 120 with one or more signal environments. The observer electronic device 120 may interact with the signal environment by detecting wireless signals around the environment. For example, the observer electronic devices 120 may detect wireless signal from a target device 121 and other wireless signals from signal clusters (also sometimes referred to as, "hyperclusters" and/or "proximal groupings of electronic and/or wireless devices") 124a, 124b, 124c, 124d. The analytic server 102 may store the interactions information into the database 104. Based on these interactions, the analytic server 102 may determine the location of the observer electronic device 120. Assuming the observer electronic device 120 is in proximity to the target device 121, the analytic server may determine the location of the target device 121. In particular, the analytic server 102 may determine the hyperclusters the observer electronic device 120 detected. As the target device 121 moves, the observer electronic device 120 that detects the wireless signals emitted from the target device 121 may detect different hyperclusters within the same geolocation or from different geolocations. For example, signal clusters 124a, 124b may be co-located at the same or nearly same geolocation 130a. Furthermore, signal clusters 124c, 124d may be co-located at the same or nearly same geolocation 130b. As shown herein, the analytic server 102 may observe four changes in signal context: hyperclusters 124a, 124b, 124c, 124d. However, these four hyperclusters may be associated with two geolocations 130a, 130b. In other words, the same geolocation may include multiple hyperclusters with each hypercluster corresponding to a micro-location within the same geolocation. Thus, the hyperclusters may be able to provide more accurate and fine-grained location information. For example, hyperclusters may be sufficient to identify a specific location in a tall building while geolocation of a tall building may not be sufficient.

When the analytic server 102 receives a request indicating that the target device 121 is lost, the analytic server 102 may locate the observer device 120 that detects wireless signals emitted from the target device 121 based on the signal environment the observer electronic device 120 is in. The analytic server 102 may receive the request to find the a target device 121, and receive observation data from the observer electronic device 120 or a plurality of other electronic devices (not shown) that observe/sense wireless signals emitted from the target device 121. Based on the observations comprising the wireless signal from the target device 121 and other wireless signals within the environment, such as wireless signals from a BLE transmitter 122a and a Wi-Fi router 122b, the analytic server 102 may determine, for example, that the observer electronic device 120 and the target device 121 are proximately located and in the signal context of hypercluster 124c, and in some cases, within a geolocation 130b.

Furthermore, the analytic server 102 may perform a resolution of the wireless signals from the BLE transmitter 122a and/or the Wi-Fi router 122b within hypercluster 124c to assign semantic meanings or atoms to the wireless signals. The semantic meanings or atoms may be knowledge on a given signal in terms of business, manufacture, function, location, and the like. Such wireless signals may provide more information on the location or environment the target device 121 is located in. For example, the analytic server 102 may resolve the wireless signals from the BLE transmitter 122a and the Wi-Fi router 122b within hypercluster 124c. The resolution results of the wireless signals may include the location, business, and any other knowledge associated with the wireless signals. For example, the resolution results may indicate that these signals are from a coffee store (e.g., Starbucks®). Such information may further narrow down the mobile device's location. For example, based on the geolocation, the analytic server may be able to determine a specific building; based on the semantic meanings (e.g., business), the analytic server may be able to determine a specific store in the building.

Figure 2:
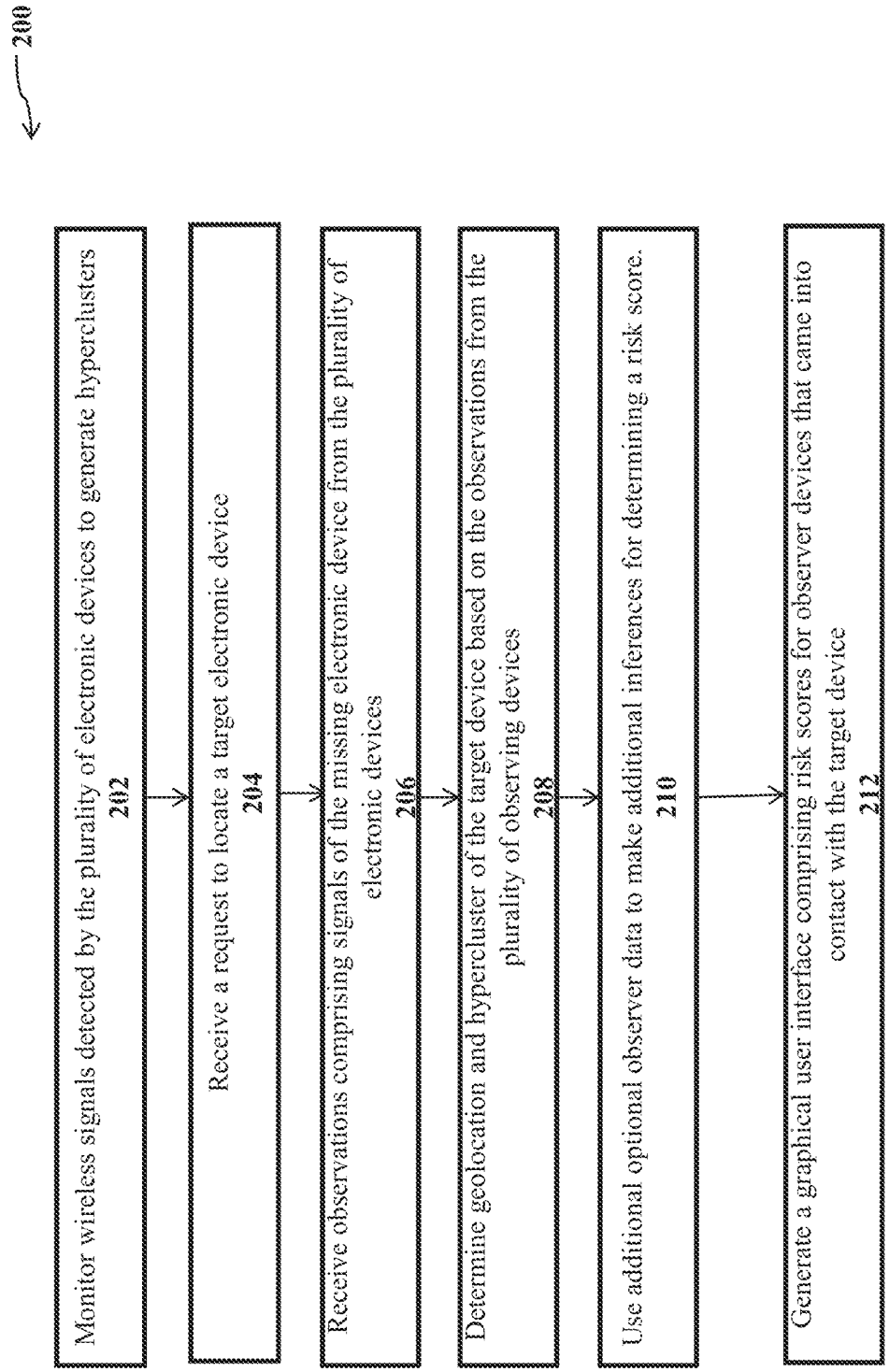
FIG. 2 illustrates a flowchart for tracing and locating electronic devices, according to an embodiment.

FIG. 2 shows a flow diagram 200 of a method for tracing and locating electronic devices, according to an illustrative embodiment. Other embodiments may comprise additional or alternative operations, or may omit some operations altogether. Although multiple computing systems and databases can implement one or more operations of the method, this description details, for brevity, an analytic server implementing the various operations of the method.

At operation 202, the analytic server may monitor wireless signals detected by a plurality of electronic devices to generate hyperclusters (also referred to as proximal groupings of wireless devices). In operation, the analytic server may trigger a signal scanning function on the electronic devices. An electronic device may be a mobile device (or handheld computer) that is portable enough to hold and operate in the hand. Typically, any handheld computer device will have a liquid-crystal display (LCD) flat screen interface, providing a touchscreen interface with digital buttons and keyboard or physical buttons along with a physical keyboard. Many such devices can connect to the Internet and interconnect with other devices such as car entertainment systems or headsets via Wi-Fi, Bluetooth, cellular networks or near field communication (NFC). Mobile devices may run mobile operating systems that allow third-party apps specialized for said capabilities to be installed and run. In the embodiments disclosed herein, the users of the electronic devices may install a software application from a vendor and the analytic server may receive the notifications from one or more servers of the vendor. The installation of the software application may trigger a signal scanning function on the electronic devices. The signal scanning function may enable the electronic devices to detect different wireless signals around the electronic device. The wireless signals may comprise Wi-Fi, Bluetooth, and Bluetooth Light (BLE). The installation of the software application may also trigger the electronic devices to transmit the detected wireless signals to the analytic server. For instance, the electronic devices may transfer a tuple of (name, MAC_address, type) for the detected signals.

The analytic server may monitor wireless signals detected by the plurality of electronic devices. The analytic server may collect the wireless signals detected/observed by the electronic devices at different time points. In some embodiments, the plurality of electronic devices may also report the geolocation data, such as latitude and longitude coordinates of where the observation is recorded. The analytic server may store the observations of the wireless signals and the geolocation data (if available) into a database.

The analytic server may collect the wireless signals detected/observed by the electronic devices at different time points periodically. For example, the analytic server may query the detected wireless signals from the electronic devices every minute. The analytic server may monitor the electronic devices for a predetermined time window (e.g., a sliding window). For example, the analytic server may monitor the electronic devices for seven days or three months.

The analytic server may monitor a given population of electronic mobile devices (users). Each electronic mobile device reports the detected signals to the analytic server. Let S denote a set of signals observed by the given population of mobile devices. As described above, a signal s may be a tuple (name, MAC_address, type). The analytic server may consider two signals to be equivalent if all three elements are equivalent. Each mobile user may be identified with a mobile advertising identifier, sometimes abbreviated as adid. Different adids may represent different mobile phones and users. Each adid may be associated with a matrix of signals and time points. Each row is a signal in S, while time points T are of minute precision, and may be closed by a given time window for the analysis. The analytic server may construct a sparse Boolean matrix, $U \rightarrow \text{Bool}^{S \times T}$ to store which signals the mobile adid u observed in the given time window. If a mobile device observed a signal s at time t, the analytic server may set the corresponding element in the matrix to 1; otherwise, set the element to 0.

In some embodiments, electronic devices report time points that may become stale over a few days. Whether or not this is indicative of nefarious behavior, doing time-dependent signal analysis on an observer's (e.g., the mobile phone's) signal observations may be difficult for the analytic server if their times are overly stale. If an observer had a signal observation that stretches credulity (the threshold set at more than five days lag), the analytic server may remove that observation (e.g., the detected wireless signals). In some embodiments, the analytic server may remove from consideration an observer (e.g., mobile device) with two or more incredible time points.

The analytic server may analyze the wireless signals to generate hyperclusters. More specifically, the analytic server may analyze the wireless signals collected at different time points from different electronic devices to build the signal graph and generate a set of hyperclusters (or signal clusters) based on the spatial proximity and temporal persistence of the wireless signals. The analytic server may save the signal graph, the hyperclusters, and corresponding geolocation data into the database.

As discussed above, the analytic server may build the signal graph that connects signals and observations into a network. The signal graph may comprise signals and observers (e.g., observer devices that observe the signals) at different time points. The analytic server may generate a set of hyperclusters (or signal clusters) based on the spatial proximity and temporal persistence of the wireless signals. A hypercluster may be a set of signals that have been observed together within a number of observations. A given hypercluster may represent a set of devices that remain in physical proximity over time. In other words, a hypercluster is a static relationship between signals, as the proximity persists across time and observations. The hyperclusters may provide useful information (e.g., location) on the physical world in terms of signals. The analytic server may utilize such information to determine the movement or location changes of a mobile device.

At operation 204, the analytic server may receive a request to locate an electronic device. The request may comprise the identifier of the target device. The identifier may be BLE standard unique identifier. Alternatively, the identifier may be MAC (media access control) address. In operation, a user may open a website in an Internet browser or a local application on an electronic client device configured to receive a request from the user. The analytic server may display a graphical user interface (GUI) for the user to input the request. For example, the user interface may include a text-based interface where the user can manually type requests and provide identifiers of target devices using a keyboard. In another example, the user interface may include an audio-based interface where the user can issue requests by verbally requesting a service.

In some embodiments, instead of looking for an electronic device, the analytic server may actively monitor the electronic device and report the locations of the electronic device by triggering an electronic message. In operation, the analytic server may provide the option to turn on or turn off an alert-triggering mechanism in the GUI. When the user turns on the alert-triggering mechanism, the analytic server may either periodically report the locations of the electronic device or trigger alert electronic messages when the device is acting out of pattern, or has moved out of a safe zone. For example, the analytic server may determine the changes of the hyperclusters of the electronic device, and transmit an alert electronic message when the changes of the hyperclusters satisfy a threshold. The alert electronic message may be proactive messages including instant messages, SMS, emails, text message, phone calls, and the like. More specifically, the analytic server may monitor the signal environment (e.g., hyperclusters) of the electronic device and determine the locations of the electronic device based on the observations from a plurality of observer devices that detect the wireless signals emitted by the electronic device. The analytic server may periodically report the locations of the electronic device. Alternatively, the analytic server may determine if the electronic device is acting out of pattern by determining how likely the device has changed dramatically, and only trigger an alert when the electronic device is acting out of pattern. However, the device may act out of pattern legitimately. For example, a luggage with BLE communication capability may be in home most of time, and start acting out of pattern when the user is travelling. The analytic server may need to be able to determine that such out of pattern actions are legitimate based on the user's reaction to the alert electronic message. In some embodiments, an administrator may configure the system and user devices to only operate within a predefined geofence based on configuration settings (sometimes referred to as, "configuration data") of a polygon. That is, the configuration settings instructs the device to begin transmitting the observation data only when it is within a virtual parameter as defined by the configuration settings of the polygon.

In some embodiments, an administrator may configure the system and user devices (e.g., observation devices) to only operate within a predefined geofence based on configuration settings of a polygon. That is, the system instructs the device to begin transmitting the observation data only when the device is within a virtual parameter of the polygon.

At operation 206, the analytic server may receive observations comprising the wireless signals emitted by a target electronic device from the plurality of electronic devices. The plurality of electronic devices may act as a network of sensors or observers for the target device. The analytic server may monitor wireless signals detected by the plurality of electronic devices by continuously receiving the wireless signals. Once the analytic server receives the request to trace interactions involving a target device, the analytic server may retrieve observation data including the wireless signals detected by different devices and determine which devices sensed the wireless signals emitted by the target device. The observer devices may also observe other wireless signals around the environment. The analytic server may further analyze the observations from such observer devices to determine, for example, the location information.

An observation may comprise detected Wi-Fi, Bluetooth, and/or BLE signal identifiers, including SSID (e.g., signal name), MAC address and/or universally unique identifier (UUID), tech (Wi-Fi, Bluetooth, BLE) and RSSI (relative measure of signal strength). Each observation may also include the following fields: token, a unique key provided by the analytic server to the app developer; ID, such as Google adid or iOS idfa (advertising identifier), the pseudorandom, resettable advertising identifier attributed to a smartphone by its operating system; the freshest available latitude/longitude reading from the smartphone; timestamp, data and time of the observation; metadata including SDK (software development kit) version, app name, device model and manufacture, and a tag assigned to the app by the developer. Assuming the observer electronic devices are within the same location of the target device, the analytic server may leverage the observer electronic devices to determine the extent of interactions between the devices of the target device (e.g., distance, duration), and thus infer the amount of contact and exposure between humans who are associated with those observer devices. The analytic server may query and refresh the observation input from the observer devices as frequently as possible or may receive a stream of observation data from the observer devices via one or more networks.

At operation 208, the analytic server may determine the observer device that were in contact with, and in some cases a geolocation or a hypercluster, of the target device based on the observations from the plurality of observer devices. The observation of each observer device may comprise the wireless signals of the target device and other wireless signals from the surrounding environment. As discussed above, the analytic server may build hyperclusters based on the monitoring of the plurality of electronic devices. Based on the observations from the plurality of observer devices, the analytic server may determine the signal context, such as hypercluster, of the target device by determining the hypercluster of the observer devices that detect wireless signals from the target device. For example, the analytic server may query the list of detected wireless signals from the observer devices and determine the corresponding hypercluster. In some other embodiments, the analytic server may be able to receive the geolocation directly from the observer devices when GPS (global positioning system) data is available.

The hypercluster may provide information on the signal environment of the target device and relevant observer devices, and further provide information on the physical environment, such as, for example, the intensity (e.g., business) that observer devices are seen at a location (in a hypercluster), or the geolocation of traced interactions. Because a hypercluster may be a set of signals that have been observed together within a number of observations, a given hypercluster may represent a set of devices that remain in physical proximity over time. In other words, a hypercluster may correspond to a physical location of note, such as a particularly busy public space or an employee's office. The analytic server may determine the physical location based on the hypercluster. For example, the analytic server may retrieve a database storing the hyperclusters and the corresponding locations.

In some embodiments, the analytic server may monitor the plurality of electronic devices, build the signal graph, and analyze the wireless signals from the plurality of electronic devices in the signal graph to determine the hyperclusters in an on-demand mode, which may provide results that are more precise. In some other embodiments, the analytic server may determine the hyperclusters in a streaming mode, for example, the analytic server may build the hyperclusters per day.

At operation 210, the analytic server may optionally use additional types of data or calculations to, for example, determine a geolocation a traced interaction or determine the user was in a particularly busy location or hypercluster based on observation data indicating semantic meanings of the wireless signals of the hypercluster. The analytic server may perform resolution of the wireless signals to assign semantic meanings or atoms to the wireless signals based on, for example, predetermined data values corresponding to observer identifiers. The semantic meanings or atoms may be knowledge on a given signal in terms of business, manufacture, function, location, and the like. Such wireless signals may provide more information on the location or environment the target device interacted with another observer device. The additional data or calculations may, for example, result in the analytics server identifying weights or business rules associated with a given location or hypercluster that are then referenced when calculating a risk score for the observer device that came into contact with the target device.

For example, the analytic server may resolve the wireless signals of the hypercluster. The resolution results may indicate that these signals are from a coffee store (e.g., Starbucks). Such information may further narrow down the mobile device's location. Based on the geolocation, the analytic server may be able to determine a specific building; based on the semantic meanings (e.g., business), the analytic server may be able to determine a specific store in the building.

The analytic server may return the following data regarding the target device: freshness, date and time of last observation; latitude/longitude, freshest reported latitude/longitude coordinates; cluster, identifier information about wireless signals observed in proximity to the targeted device, atoms, attributes for signals within the cluster to describe a venue or location (e.g., Starbucks).

At operation 212, the analytic server may generate a graphical user interface on the electronic client device comprising risk scores for the observer devices that were in contact with the target device, and in some implementations, location information of the target device. The output may include, for example, observer identifiers, employee names, a risk score, or a risk tier for each of the observer devices.

In some embodiments, the analytic server may work with a third-party server, such as a third-party company, to trace the locations of devices associated with the third-party company. The analytic server may receive a request from the third-party company to find one of its devices, perform the analysis to determine the device's location, and send the output of the device's location to the third-party company. The third-party company may then generate a graphical user interface via an app from the third-party company on a user's device. In other words, the analytic server may transmit the location information directly to a user's device and display the GUI comprising the location information on the user's device. Alternatively, the analytic server may work with a third-party company, which is in the middle between the analytic server and the user, and transmit the location information to the third-party company.

Figure 3:
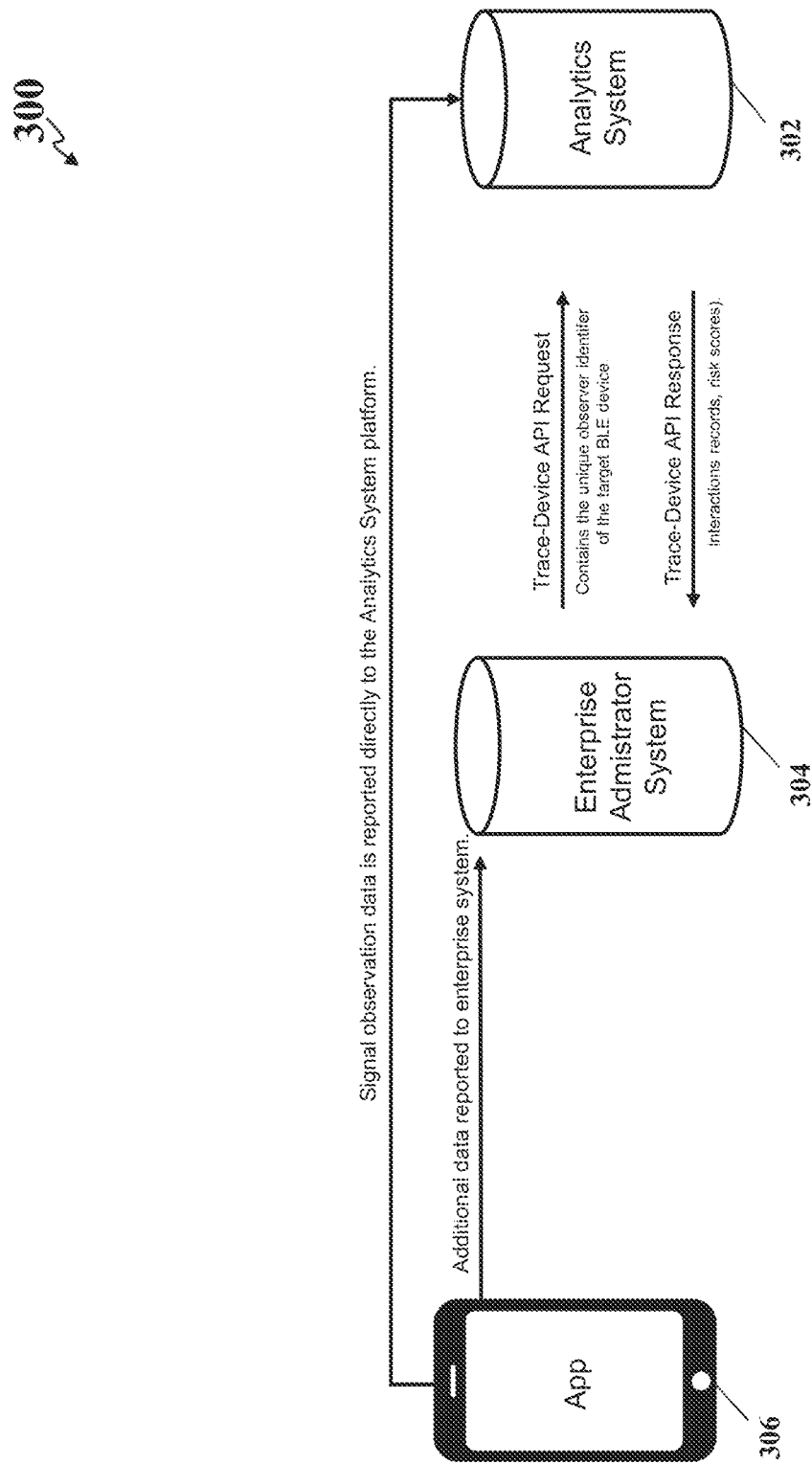
FIG. 3 illustrates an example of system architecture for working with a third party to locate electronic devices, according to an embodiment.

FIG. 3 illustrates an example of system architecture for working with a third party to locate electronic devices, according to an embodiment. In some embodiments, the analytic server 302 may work with an enterprise administration server 304, to trace interactions among electronic devices operated by the employees associated with the enterprise network or ecosystem. For example, employees may have their mobile devices 306 installed with an application ("app") containing an SDK and developed for the enterprise server 304. This app may report signal observation data to the analytic server 302. The signal observation data may comprise signals and observers (e.g., observer devices that observe the signals) at different time points. Based on such signal observation data, the analytic server may build the signal graph and generate hyperclusters. In addition, the app on the mobile devices 306 may report additional data to the enterprise server 304, such as the observer identifier, a human employee identifier, and in some cases, a health status indicator to indicate the employee has been infected. An administrator user may issue a tracing request to the third-party server 304 via a client computing device (not shown) or submit the request directly into the third-party sever 304. The request may comprise the unique observer identifier of a target device associated with an employee who has test positive for infection. After receiving the request from the administrator, the enterprise server 304 may issue a tracing request to the analytic server 302 comprising the observer identifier of the target observer device. The analytic server 302 may identify which other observer devices in the network ecosystem were in contact with the target device and calculate a risk score for those devices. The analytic server may return the risk score or contact observation information to the enterprise server 304 as a response. The enterprise server 304 may receive the location information from the analytic server 302, transmit the location information, and generate a GUI for presentation to the administrator user's computing device to display the resulting tracing information. In some embodiments, the enterprise server 304 may enrich location information with map data from another server (not shown), based on latitude and longitude data received from analytics server.

Figure 4:
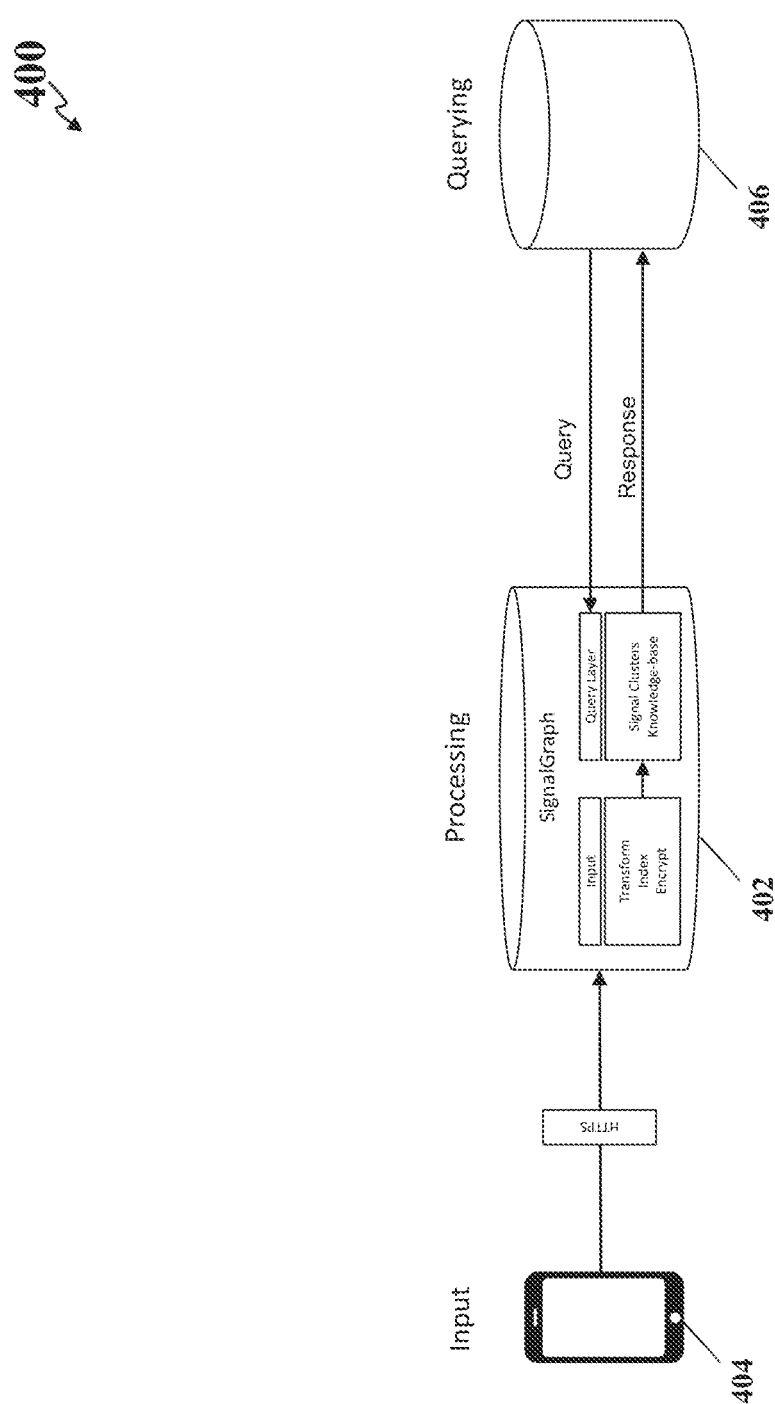
FIG. 4 illustrates a first example of data flows for locating electronic devices, according to an embodiment.

FIG. 4 illustrates a first example of data flows for locating electronic devices, according to an embodiment. The analytic server 402 may receive and collect observation data from mobile devices installed with a third-party app. The mobile devices 404 with the app may be devices operated by customers of the third-party server. The app may comprise observer SDK that collect observations of nearby, detectable Wi-Fi, Bluetooth, and BLE signal information from different devices, such as Wi-Fi hotspots, wearables, and smart-home electronics. The SDK-enabled app on mobile device 404 may report signal observation to the analytic server 402 through Hypertext Transfer Protocol Secure (HTTPS). The analytic server 402 comprising the signal graph platform may transform, encrypt, and index the input signal information (e.g., observations) into a knowledge-base. The analytic server 402 may comprise a query layer that receives a request from the third-party server 406 to find one of its devices. The analytic server may perform the analysis utilizing the combined network input and knowledge-base from the third-party server and other apps of signal clusters to determine the device's location, and send the response of the device's location to the third-party server.

Figure 5:
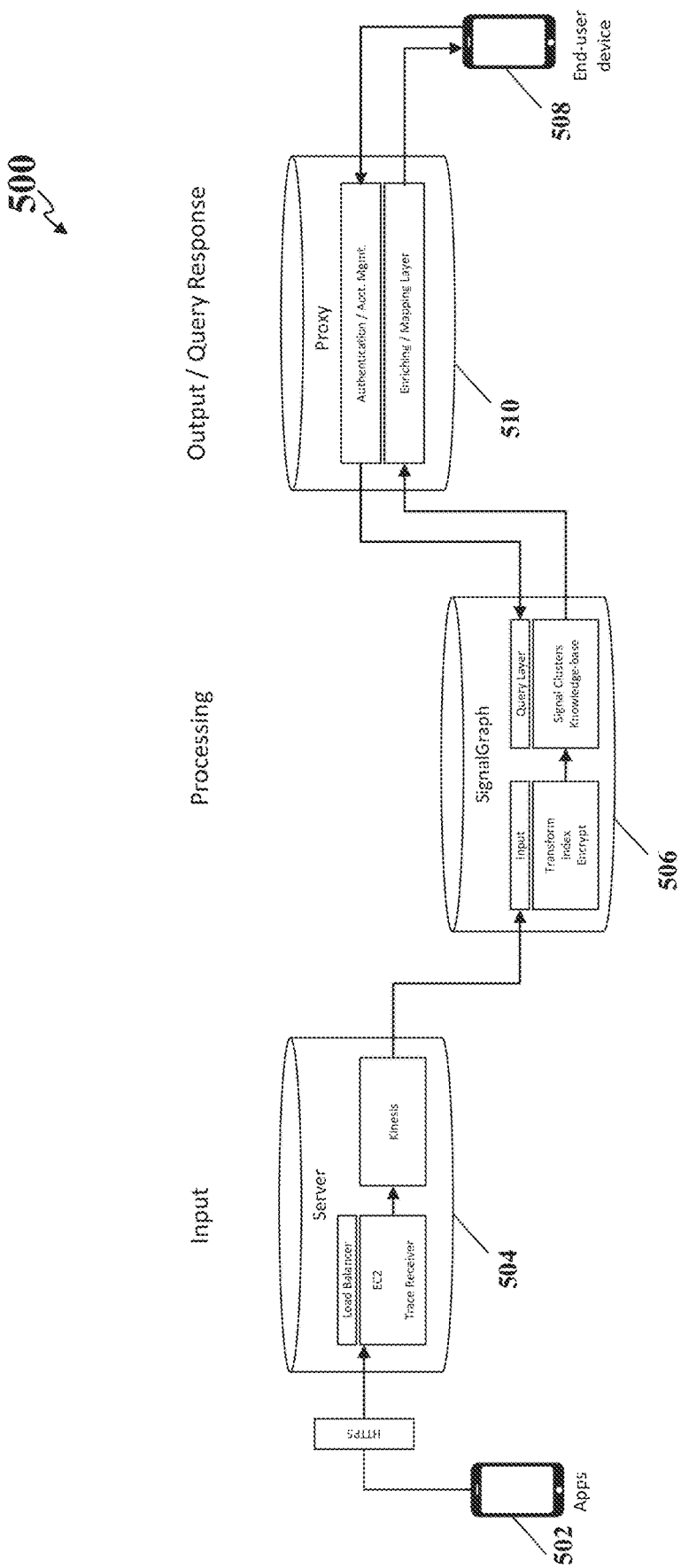
FIG. 5 illustrates a second example of data flows for locating electronic devices, according to an embodiment.

FIG. 5 illustrates a second example of data flows for locating (e.g., tracing) electronic devices, according to an embodiment. A mobile device 502 with a third-party server developed app may collect and report signal information from nearby devices (MACs, SSIDs, UUIDs), along with latitude/longitude and timestamp to a third-party server 504 through HTTPS. The third-party server 504 may validate the input and push all observations into a Kinesis queue. The Kinesis queue may hold observations for a period of time in a first come first out manner. The third-party server 504 may pass the observations (e.g., adid of smartphone, MACs, SSIDs, and UUIDs of observed signals, timestamp, and latitude/longitude, etc.) to the analytic server 506 through an observer application programming interface (API). The analytic server 506 may transform, index, and encrypt the input signal information (e.g., observations) into signal clusters. An OEM (Original Equipment Manufacturer) app end user may input a locate request (e.g., find-device request) on a user device 508. A proxy server 510 may perform request management for account authentication, and forward the request to the analytic server 506. The analytic server 506 may comprise a query layer that receives the request. The analytic server 506 may perform the analysis utilizing the combined network input and knowledge-base from the third-party server and other apps of signal clusters to determine the device's location. The analytic server 506 may return a response comprising freshest signal cluster, location, and timestamp. The proxy server 510 may enrich the response on mapping layer to include enriched location, POI and address information, and return the response to the end user device 508.

II. Generating Graphs of Communications & Groupings

A server can receive or otherwise extract communication records from across any number of communications tools or services (e.g., Gmail®, Slack®, Skype®, Git®). The server identifies and executes appropriate conversion software modules based on the source communication tools for the communications records. The conversion modules convert the communication records for each of the enterprise users into normalized or otherwise compatible data record format, which can be stored into one or more databases. These converted or integrated data records can include various data fields or labels indicating certain information about the communications, users, past projects, and current projects. The server can execute various processes for generating a graph data structure based upon the converted data records. One having skill in the art will appreciate that graphs are not necessarily visual representations, but rather are a data structure having a set of objects (sometimes called "vertices" or "nodes") that are related according to one or more communications patterns of the users, which would serve as the edges of the graph and the clusters. The server may perform various clustering techniques, such as those previously discussed with respect to hyperclustering, to derive clusters of users who are communicating together and thus forming or operating as teams. The hyperclustering operations (as discussed above with respect to clustering using wireless signals) may be applied to the communications data records to effectively generate, identify, and characterize projects teams. The server may analyze additional data inputs or labels, such as the results of prior projects, to determine, for example, successful communication patterns, bottom-up teams, and inter-team knowledge sharing facilitators. The server would then apply the communication patterns, as the edges that exist in these clusters, as well as the other data inputs would to generate the proposed team of users for a new project.

A server may analyze communication data generated from across a plurality of communication tools (e.g., Skype®, email) associated with one or more prior projects. Using this data, the server may determine from all the people involved, who is actually communicating with respect to the project or who is contributing to team morale, and what is the amount of that communication. Each interaction of a conversation or the entire conversation can be represented as an edge of a graph. By analyzing the communication data associated with these edges, the server can determine various characteristics of the interaction, conversation, and/or users, and identify, for example, which users are contributing interactions that are topically relevant to the ongoing project. Likewise, the server can identify which users are not particularly engaged.

Illustrative System

Figure 6:
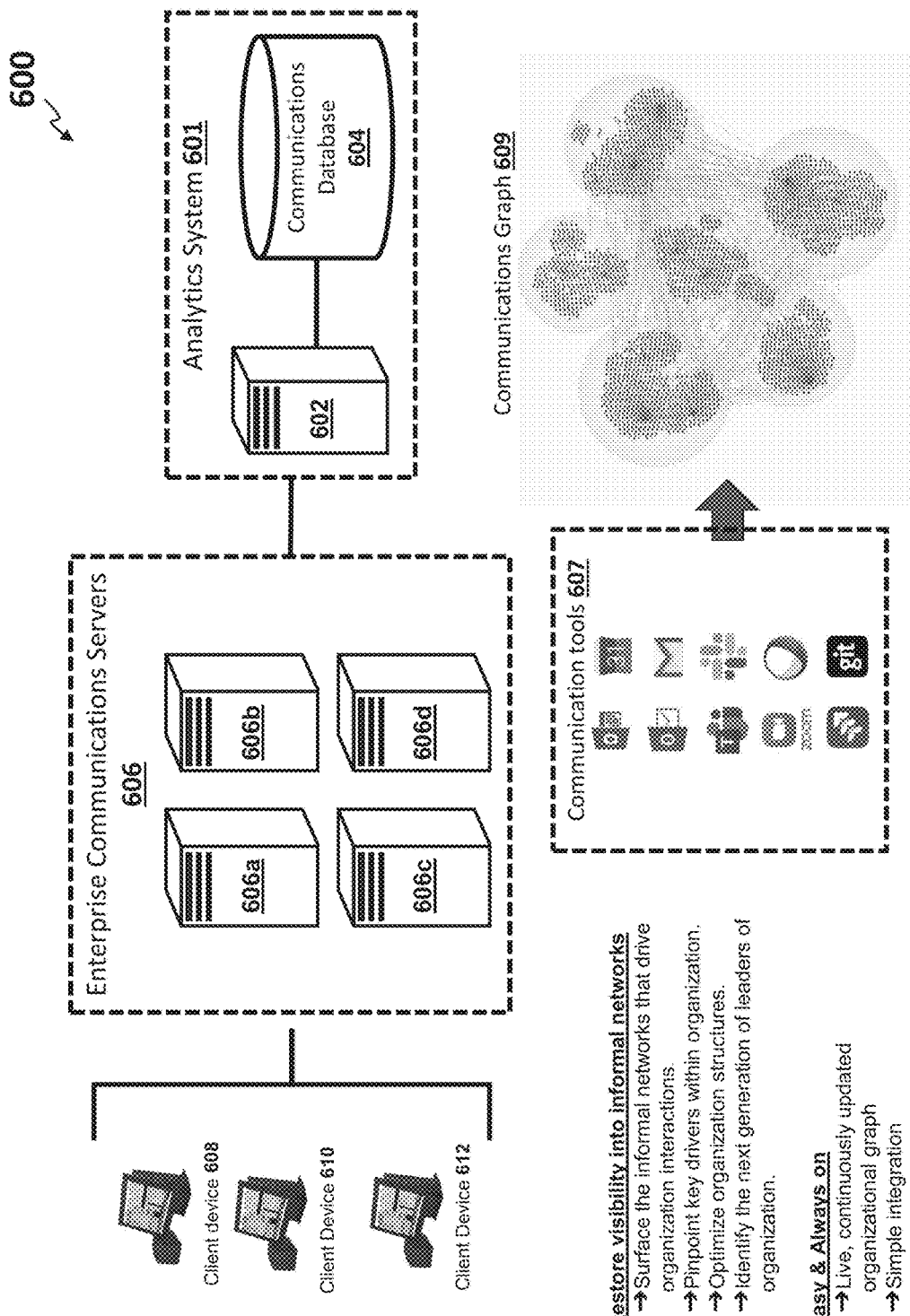
FIG. 6 shows components of an illustrative system according to an embodiment.

FIG. 6 shows components of a system 600 according to an embodiment. The system 600 includes an enterprise infrastructure comprising communication servers 606 that host communication tools 607 allowing employees to communicate and collaborate with one another and facilitate remote work. Non-limiting examples of communication tools 607 include Slack®, Teams®, Google®, Gmail®, Google G-Drive®, Microsoft One Drive®, and the like. The communication tools 607 each include simple APIs or conversion modules through which an analytics server 602 can issue queries to current or historic data records having the data and metadata for users exchanging information using the various tools 607. These APIs may also be used by the servers 606 to interchange communications data across the servers 606 or to ingest communications data from the servers 606.

The enterprise communications servers 606 comprise any number of computing devices that host communications tools 607, which are software applications employed by users of an enterprise system 600. The communications servers 606 may be internal or external to the enterprise infrastructure. Likewise, the communications tools 607 may be hosted on servers 606 internal to the enterprise infrastructure or be hosted on servers 607 of a third-party. The communications tools 607 may be any enterprise software program that facilities various types of communication (e.g., unified communications application, instant messaging application, email), project management, or project collaboration. Users operate the communications tools 607 using client devices 608, 610, 612, which access the communications servers 606 over one or more internal and/or external networks. As shown in FIG. 6, non-limiting examples of communication tools 607 may include Microsoft Outlook®, Microsoft Exchange®, Microsoft Teams®, Zoom®, Git®, Google Gmail®, Google Calendar®, Cisco Webex®, Slack®, and the like. The communication tools 607 output communications data of various different forms, such as user work product (e.g., documents), communications logs, and the like. The communications data may be stored into various machine-readable storage media accessible to an analytics server 602.

The analytics server 602 is a computing device that executes various data conversion modules for each of the communication tools 607 and analyzes the communication data stored and extracted from the servers 606 hosting the communication tools 607. The analytics server 602 uses the communications data to build a graph 609 representing which users or client devices 608, 610, 612 are communicating with other users or client devices 608, 610, 612. The analytics server 602 and other devices of the system 600 may store, retrieve, and output various types of data to a communications database 604. For example, the analytics server 602 can store into the database 604 the various communications data records that the analytics server 602 has converted from the formats of communication tools 607 to the format compatible with the operations of the analytics server 602. As another example, the analytics server 602 may store the graph and other output of the analytics operations into the database 604.

The database 604 stores the converted records generated by the analytics server 602. The converted records stored in the database 604 may be associated with the users of the system 600. The database 604 may further include data records that are associated with, for example, past projects, communications tools 607, and client devices 608, 610, 612, among other types of data. The data records may include one or more labels indicating quality or success metrics for current or prior projects.

In operation, the analytics server 602 may generate or identify the labels indicating the quality or the success metrics for current or prior projects. The analytics server 602 may derive properties of each user or the projects; non-limiting examples of such properties may include the communication tools 607 employed by the users, identifiers and characteristics of the prior projects that users were involved with, and user communication patterns, among others. The analytics server 602 can reference and use such data to generate a graph 609 of users or projects, which the analytics server 602 uses to generate groupings of possible teams or team members. In some embodiments, the analytics server 602 generates a separate data structure for the graph 609. Additionally or alternatively, in some embodiments the data records of the database 602 include data fields intended to interrelate the data records, such that the data records effectively represent the graph 609 data structure.

The analytics server 602 can analyze the graph 609 to determine, for example, which users are frequently in communication with each other and the projects that involved the communications data for those user, and determine an impact, character, or role for each particular user across the communication data for one or more prior projects. For example, the analytics server 602 may determine whether users tend to work in teams where there is a lot of communication or the opposite. As another example, the analytics server 602 can determine which team members are the "glue" socially, who keep the projects, teams, or other aspects of the organization socially interconnected. In this example, the graph indicates to the analytics server 602 users who connect users, are very engaged on projects, and contributes to teams assembled for prior or current projects.

Illustrative Method of Converting Communications

Figure 7:
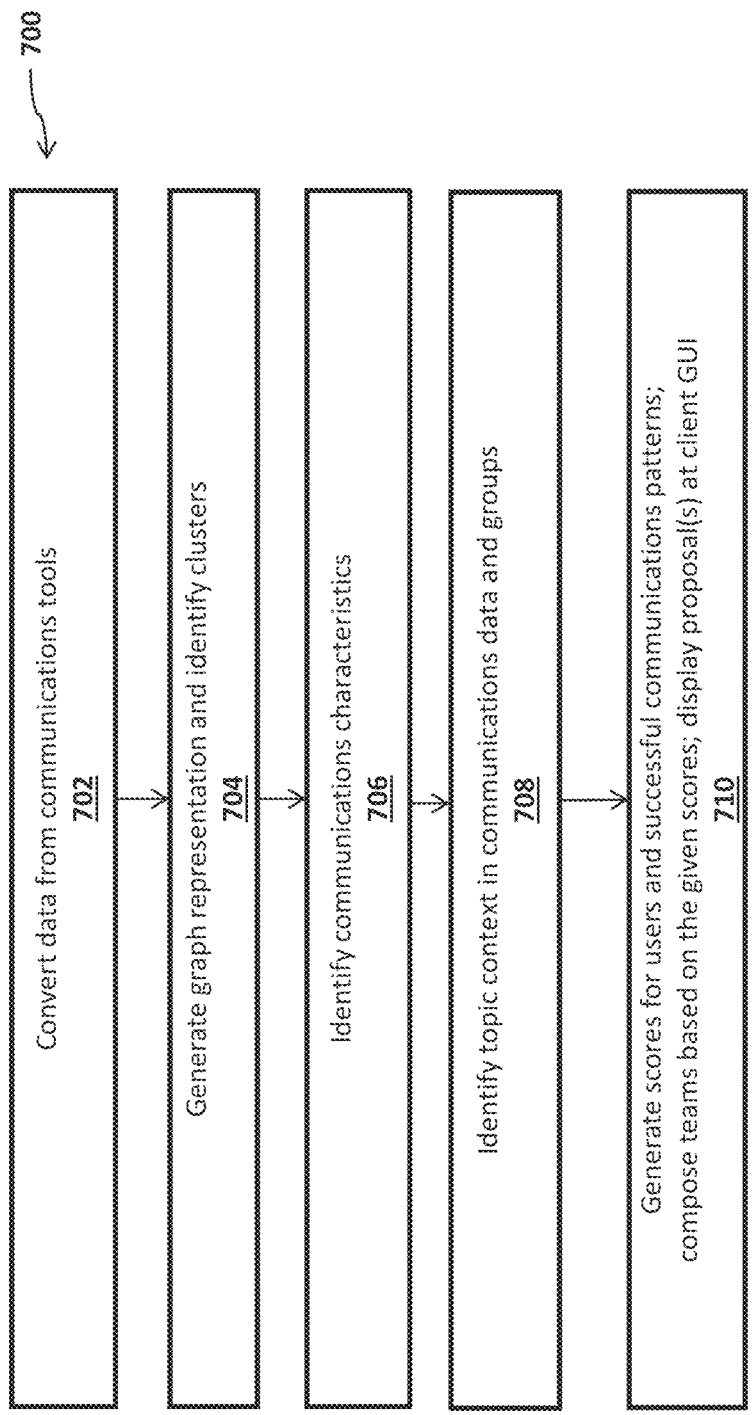
FIG. 7 shows execution steps of an illustrative method according to an embodiment.

FIG. 7 shows execution steps of an illustrative method 700 according to an embodiment. The steps of the illustrative method 700 are executed by a server, such as the analytics server 602 of FIG. 6, though the method 700 may be performed by any number of computing devices. It should also be appreciated that other embodiments may comprise additional or alternative steps or may omit certain steps, yet still fall within the scope of this disclosure.

In a first step 702, a server executes connector programs to query and convert communications data outputted or otherwise generated by communication tools. The server may execute the connectors at a given interval (e.g., every minute, hourly, daily) or in response to certain triggering conditions, such as a request from a client device. The connectors effectively call or query the various types of communication data from the communication tools and converts the communications data into converted data records containing the communications data in a format compatible with the server analytics operations. In some implementations, the server may also store the converted data records into a communications database.

In some implantations, for each communications channel or tool (e.g., Slack®, Teams®), the server identifies in the communications data from users who are in active or routine communication within a certain sliding time window (e.g., 5 minutes). The sliding five-minute windows would capture who is actively communicating. For emails, the server would use a similar approach, identifying, for example, who is replying to whom in an email chain, where the email chain itself would have timestamps spanning a given window (e.g., 5 hours). The analytics server would determine, from the communications data, who has actively contributed to the email chain. The sliding window beneficially avoids the pitfalls of what happens when an email chain, for example, has many contributors or many recipients. As such, the sliding window may function as filter of passive participants. For group chats or conference meetings in unified communications or teleconferencing applications (e.g., Skype®, Webex®, Zoom®), there may be a chat or meeting of many participants, though only a small number of contributors. The sliding window can be used to filter communications data for only the data related to contributors.

In a next step 704, the server builds a graph data structure using from the communications data retrieved and converted. After the conversion, the server would derive the basic edges of the graph that represent who is communicating with whom. The graph is generated based upon identified edges and hyper-edges, which correspond to the observed communication patterns in the communication data, such as communication instances (e.g., emails, instant messages). The server generates the graph using the communications data and applies the clustering techniques to the data records, such as the techniques described above used to derive hyper clusters of devices from wireless signals. The server derives clusters of users who are communicating with one another and thus likely forming a team.

The database contains data for instances when users, who may be team members of prior or current projects, are exchanging information, as converted or translated from a relatively unstructured communication medium of various communications applications, such as email chains, and from channels, such as Word® files in Microsoft One Drive® that may have a lot of users who can access them but in reality only three or four people actually read the file, contribute to the file, and use the file to exchange information.

The server places all the nodes (denoting users or user devices) and the edges (denoting communication activity) into a graph, where an edge can be labeled with, for example, a particular topic, particular style of communication or other communication attributes, which tool was used, and the like. As the time unfolds the server populates the graph with information represented as time-sharded edges. The server may then determine normal or expected communication patterns, which may be associated with users and projects. Once the graph is generated, then the server derives one or more vectors from hyperclusters associated with every node (user) and every project (sub-graph).

In a next step 706, the server identifies and generates certain characteristic information about the communications or edges, indicating some characteristic about the communication instance itself.

As an example, an instant communications application (e.g., Slack®, Skype®, Teams®) may be commonly employed by technical development teams to exchange a lot of communication that is very technical and related to solving a particular engineering problem. In this example, the communications can be characterized via labels or data fields as being, for instance, particularly content-heavy or project-oriented. In another example, there may be a lot of communication instances that include an emoji, a gif, or information otherwise not technical or contributing to the solution itself. These communications may not be particularly project or solution-oriented, but these communications can represent socially relevant interactions for team building and morale purposes. For example, communication data for an interaction or conversation may include more words that are technical or formal in nature, or an emoji or information language, then the computer may classify the conversation or interaction accordingly. This information may become an edge or a component of an edge.

Classification may be based upon heuristic rules and/or trained classifiers. For example, selected English words may represent informal social interactions based on a corpus of informal conversations. For instance, if 50% of the nouns constitute informal or non-engineering related interactions, then such conversations would be classified as a social interactions.

In step 708, the server identifies one or more topics of the communications instances from the context of the communication data the technical communication in terms of topics. When the server determines that the participating users of a conversation (e.g., instant messaging session, email chain) were discussing an engineering problem, then the server determines the topics within that conversation. In some embodiments, the server may execute natural language processing (NLP) algorithms against a content portion of the conversation data to understand what was being discussed.

In step 710, the server generates one or more scores for each user and for each project. These scores are derived from vector comparisons between users and projects. The scores generated by the server indicate who has contributed to a mixture of, for example, regularity of interactions, social glue, technical conversations, and the variety of topics discussed. Given these scores, the server can determine the thresholds that denote successful projects, and good communicators and communication patterns. Finally, the server can use the aforementioned scores to determine which users would be good additions to a given project team.

The scores effectively represent measures for various characteristics of conversations or communications patterns, such as relevant topics, communications tool(s) employed, when people interact, frequency of the interactions, certain times of the day, topics discussed, personal or socially-relevant communications.

In some embodiments, each user in the system is associated with a feature vector of all these features and then the server determines the distances between the feature vectors. For example, the server generates a feature vector for a particular user depending upon how the user employs the various communication tools. The server could then determine, for example, the users who use the tools in a similar manner as others, who could be a team leader, and other information that fits one or more models. The server can determine which users are essential for inter-team communications and knowledge sharing. The server can also suggest one or more new teams members. In some cases, the server automatically identifies the proposed team. In some cases, the propose team members may be transmitted to a GUI of an administrator user who may confirm the proposed team members. The server may also transmit to a GUI summary reports describing the characteristics of successful teams and their communication patterns. The server may perform search to find other instances of successful projects and, importantly, identify those projects that have different communication patterns indicating that they may need closer performance evaluation. As an example, for each communication medium, the server may correlate users and/or user characteristics with successful projects. The server may later reference clusters generated according to the correlations to later identify a set of one or more characteristics of communication patterns and/or users for generating a proposed project team.

The server can generate the final score to represent a similarity score between the communication behavior and/or other information. In graph terminology, the information points are often referred to as "embeddings." In operation, the server may compute a feature vector of values for the various communication patterns or other relevant aspects of the communication data, which denote how the user is using the communication tool(s)/channel(s). In some circumstances, the numbers in themselves are latent variables, and may or may not necessarily represent something in the real world. The communication data used for a feature vector may be a representational aggregation of behavior, such that the server determines that one vector represents one user and another vector represents another user. Then based upon the vector similarity, then the server can determine, for example, a first user and a second user have certain similarities and/or compatibilities in how these users communication. Using the distance between these vectors or other similarity scores, and, in some cases, one or more threshold values, the server could determine that the users could be proposed as team members.

In some embodiments, the server can generate a notification based on the feature vector, a comparison of two or more feature vectors, and/or one or more characteristics associated with a user. Accordingly, the server can generate and send a notification to a user, e.g., an administrator user. The notification can be presented to the user via a display. In some embodiments, the notification can be associated with suggested team members, automatically generated teams, final scores, successful teams and their communication patterns, and/or less successful teams (e.g., low performing teams) and their communication patterns.

In some embodiments, the system can facilitate communication between a first user and a second user that were not previously in contact. For example, the system can suggest a new member for a team based on one or more identified characteristics, e.g., based on feature vectors associated with the new member and the feature vectors associated with the existing members and/or project. In some examples, the team can be associated with a specific project. The system can then facilitate communication between the new member and existing members. For example, the system can create a new message thread, e.g., send an email or create a new group via a messaging application, including the new and existing members to introduce the new member to the team. In some examples, the system can send an email and/or notification to the team leader, thereby facilitating communication between the team leader and the new member. In some examples, the new member and existing member may not have previously been in contact. In some examples, the new member and existing members may not have previously been in contact regarding a specific project.

In some examples, the system can facilitate communication between an automatically generated team. For example, the system can create a new message thread, e.g., send an email or create a new group via a messaging application, including the members of the automatically generated team to facilitate communication between the team members. In some examples, the new team may not have previously been in contact. In some examples, the new team may not have previously been in contact regarding the specific project.

In some implementations, a server may operate in a real-time or streaming mode in which the server is actively populating a graph for one or more projects and computing one or more embeddings in real-time or near real-time. Conventional approaches to embeddings do not generate or update embeddings on-the-fly, but rather operate in a more static approach.

The server could also consider risk of project failure, as a separate risk score or as a component of another scoring algorithm. The server could receive inputs from administrative users to indicate whether the team or certain team members is/are being effective.

In some implementations, the scoring may be weighted. By default there will be no weight, so every dimension is scored equally, but if the company uses historic communication data to train a weighted model, where the historic communication data may be used by the server to indication which prior projects had effective teams. The server can use that labeled historic communication data to derive one or more weights of critical values and/or user data values. For example, the system can receive communication data associated with one or more projects to be used as training data for a machine learning model. In some examples, the system can receive data indicative of an assessment of a performance level associated with a project included in a training data set, e.g., a rating of the success or performance level of a project. In some examples, the data can be binary (e.g., high performing or low performing) or a rating (e.g., a number "x" out of ten, a percentage value, etc.). In some examples, a label for the communication data associated with a project can be generated based on the data indicative of an assessment of the performance level of the project. This training data (e.g., communication data and label) can be used to train the machine learning model. In some examples, the machine learning model can be used, in part, to determine a set of characteristics associated with successful or high performing projects. In some examples, the machine learning model can be used to derive weights for one or more characteristics associated with a project or user.

Example Use Cases

In one example, the server may be employed to identify effective remote teams versus less effective teams. Labeled data indicating which projects have been more effective, thereby labeling which communication data is associated with effective or ineffective projects. The server output a summary of characteristics of interactions and/or users that contribute to effective teams and/or user that contributes to less effective teams. The server could determine these characteristics or users for ongoing or past teams, in real time or in a retrospective view, based upon user communication data. The system would beneficially minimize the risk that remote work is negatively impacting corporate output.

In another example, administrators of the system could employ the server to identifying users for a proposed team. In operation, a server could help in team construction by suggesting users based upon user engagement and communication data in previous projects as analyzed by a trained machine learning model. In some cases, if there is an additional seed of a team (e.g., three people), then the server could predict one or more additional users who could augment the likely effectiveness of the team, based upon the communication data (e.g., topics discussed within those conversations, success of prior projects, prior interactions) of the extant members of the team and the other users. Additionally or alternatively, the server may use the communication data to determine/update a risk to a project if a user were to leave the team.

Embodiments of the present disclosure include systems and methods for generating a graph and/or data structure that includes clusters around at least one of a characteristic and a user. For example, a computer implemented method according to embodiments of this disclosure can include receiving, by the computer, communication data from a plurality of servers hosting plurality of communication tools, the communication data associated with a plurality of conversations involving one or more users. In some examples, the method can further include converting, by the computer, the communication data into a common format. In some examples, the method can further include generating, by the computer, a graph based upon the communication data in the common format based upon one or more characteristics identified in the communication data and the one or more users involved with the plurality of conversations. In some examples, the method can further include clustering, by the computer, the communication data in the graph according to the one or more characteristics and the one or more users, thereby generating one or more clusters around at least one of a characteristic and a user.

In some examples, the method can further include, for each communication medium, identifying, by the computer, a set of one or more characteristics of communication patterns correlated with successful projects according to the clusters. In some examples, the method can further include identifying, by the computer, a set of users who establish and maintain inter-team communications according to one or more characteristics of each user. In some examples, the method can further include identifying, by the computer, teams that form bottom-up in a project or across projects, and are not explicit in the organization. In some examples, the method can further include identifying, by the computer, a set of users for a project according to the clusters. In some examples, the method can further include identifying, by the computer, a characteristic of a conversation indicating a social interaction originated from a user. In some examples, the method can further include identifying, by the computer, a characteristic of a conversation indicating a topical interaction originated from a user. In some examples, the method can further include identifying, by the computer, a topic in the topical interaction originated from the user.

Embodiments of the present disclosure relate to systems and methods for determining a set of one or more identified characteristics correlated with high performing projects. In one or more embodiments, methods according to embodiments of the present disclosure can include receiving, by the computer, communication data from a plurality of servers hosting plurality of communication tools, the communication data associated with a plurality of conversations involving one or more users. In some examples, the methods can further include converting, by the computer, the communication data into a common format. In some examples, the methods can further include generating, by the computer, a graph based upon the communication data in the common format based upon one or more characteristics identified in the communication data and the one or more users involved with the plurality of conversations. In some examples, the methods can further include clustering, by the computer, the communication data in the graph according to the one or more characteristics and the one or more users, thereby generating one or more clusters around at least one of a characteristic and a user. In some examples, the methods can further include generating user data for each of the one or more users based on the one or more clusters. In some examples, the methods can further include generating project data for one or more projects based on the one or more clusters. In some examples, the methods can further include determining, by the computer, the set of one or more identified characteristics correlated with high performing projects, based on the user data and the project data, the one or more characteristics associated with the user data or project data.

In some embodiments, the one or more identified characteristics include one or more selected from: communication tools, users associated with a conversation, users actively participating in the conversation, time of day associated with the conversation; or a topic of the conversation. In some embodiments, the method can further include identifying, by computer, one or more topics associated with the plurality of conversations, wherein the one or more topics relate to a technical aspect of a respective project, where identifying the set of one or more characteristics is performed based on the one or more topics. In some embodiments, the method can further include identifying, by the computer, one or more sub-groups associated with a project, wherein each sub-group comprises one or more users associated with the project and associated with a communication activity that relates to a particular topic, where identifying the set of one or more characteristics is performed based on the one or more sub-groups.

In some embodiments, the method can further include, for each communication tool, identifying, by the computer, a set of one or more characteristics of communication patterns correlated with high performing projects based on the user data and the set of one or more identified characteristics. In some embodiments, the method can further include identifying, by the computer, a set of users who establish and maintain inter-team communications according to one or more characteristics of each user. In some embodiments, the method can further include identifying, by the computer, teams that form bottom-up in a project or across projects, and are not explicit in the organization. In some embodiments, the method can further include identifying, by the computer, a set of users for a project based on the user data and the set of one or more identified characteristics.

In some embodiments, the method can further include updating, by the computer, a data structure representing the team members corresponding to the project based on the set of one or more identified characteristics. In some embodiments, the method can further include facilitating, by the computer, communication between a first user and a second user that were not previously in contact, based on the set of one or more identified characteristics. In some embodiments, the method can further include causing display of a graphical user interface that includes the set of one or more identified characteristics.

In some embodiments, the method can further include generating a notification based on the set of one or more identified characteristics and causing the notification to be presented via a display. In some embodiments, the method can further include identifying, by the computer, a characteristic of a conversation indicating a social interaction originated from a user. In some embodiments, the method can further include identifying, by the computer, a characteristic of a conversation indicating a topical interaction originated from a user. In some embodiments, the method can further include identifying, by the computer, a topic in the topical interaction originated from the user. In some embodiments, the method can further include identifying a project that lacks a characteristic identified in the set of one or more identified characteristics, identifying a user of the one or more users associated with the lacking identified characteristic; and recommending the user for the project.

In some embodiments, the method can further include determining, by the computer, a risk score indicative of a risk of failure of a project, based on the user data and the project data. In some embodiments, the one or more communication activities corresponds to one or more of a conversation topic, a communication style, or a communication tool.

In some embodiments, identifying, by the computer, the set of one or more characteristics correlated with successful projects can include determining user scores for each user of the one or more users, determining project scores for each project of the one or more projects and identifying one or more high performing projects based the project scores and the user scores. In such embodiments, the method can further at least one of the user score or project score is indicative of at least one selected from: relevancy of discussion topics, use of communication tools, timing of interactions, frequency of interactions, contributions to technical conversations, or socially relevant communications. In such embodiments, identifying one or more high performing projects comprises comparing, by the computer, a project score associated with a particular project to a threshold.

In some embodiments, the method can further include receiving data indicating an assessment of a performance level associated with a project included in a training data set. In such embodiments, the method can further include generating a label for communication data associated with the project with the performance level assessment. In such embodiments, the method can further include training a machine learning model based on the labeled data, where determining the set of one or more identified characteristics correlated with high performing projects is based at least in part on the model.

Embodiments of the present disclosure can provide a system for determining a set of one or more identified characteristics correlated with high performing projects. The system can include one or more processors, a memory, and one or more programs. In some embodiments, the one or more programs are stored in the memory and configured to be executed by the one or more processors. In some examples, the one or more programs include instructions for: receiving, by the computer, communication data from a plurality of servers hosting plurality of communication tools, the communication data associated with a plurality of conversations involving one or more users, converting, by the computer, the communication data into a common format, generating, by the computer, a graph based upon the communication data in the common format based upon one or more characteristics identified in the communication data and the one or more users involved with the plurality of conversations, clustering, by the computer, the communication data in the graph according to the one or more characteristics and the one or more users, thereby generating one or more clusters around at least one of a characteristic and a user, generating user data for each of the one or more users based on the one or more clusters, generating project data for one or more projects based on the one or more clusters, and determining, by the computer, the set of one or more identified characteristics correlated with high performing projects, based on the user data and the project data, the one or more characteristics associated with the user data or project data.

Embodiments of the present disclosure can provide a non-transitory computer-readable storage medium storing one or more programs, the one or more programs comprising instructions. The instructions, when executed by one or more processors of one or more electronic devices, can cause the electronic devices to: receive, by the computer, communication data from a plurality of servers hosting plurality of communication tools, the communication data associated with a plurality of conversations involving one or more users, convert, by the computer, the communication data into a common format, generate, by the computer, a graph based upon the communication data in the common format based upon one or more characteristics identified in the communication data and the one or more users involved with the plurality of conversations, cluster, by the computer, the communication data in the graph according to the one or more characteristics and the one or more users, thereby generating one or more clusters around at least one of a characteristic and a user, generate user data for each of the one or more users based on the one or more clusters, generate project data for one or more projects based on the one or more clusters, and determine, by the computer, the set of one or more identified characteristics correlated with high performing projects, based on the user data and the project data, the one or more characteristics associated with the user data or project data.

Exemplary Embodiments

Among the provided embodiments are:
1. A computer-implemented method comprising:
    receiving, by the computer, communication data from a plurality of servers hosting plurality of communication tools, the communication data associated with a plurality of conversations involving one or more users;
    converting, by the computer, the communication data into a common format;
    generating, by the computer, a graph based upon the communication data in the common format based upon one or more characteristics identified in the communication data and the one or more users involved with the plurality of conversations; and
    clustering, by the computer, the communication data in the graph according to the one or more characteristics and the one or more users, thereby generating one or more clusters around at least one of a characteristic and a user.
2. The method according to embodiment 1, further comprising, for each communication medium, identifying, by the computer, a set of one or more characteristics of communication patterns correlated with successful projects according to the clusters.
3. The method according to any one of embodiment 1-2, further comprising identifying, by the computer, a set of users who establish and maintain inter-team communications according to one or more characteristics of each user.
4. The method according to any one of embodiment 1-3, further comprising identifying, by the computer, teams that form bottom-up in a project or across projects, and are not explicit in the organization.
5. The method according to any one of embodiment 1-4, further comprising identifying, by the computer, a set of users for a project according to the clusters.
6. The method according to any one of embodiment 1-5, further comprising identifying, by the computer, a characteristic of a conversation indicating a social interaction originated from a user.
7. The method according to any one of embodiments 1-6, further comprising identifying, by the computer, a characteristic of a conversation indicating a topical interaction originated from a user.
8. The method according to embodiment 7 further comprising identifying, by the computer, a topic in the topical interaction originated from the user.
9. A computer-implemented method for determining a set of one or more identified characteristics correlated with high performing projects, the method comprising:
    receiving, by the computer, communication data from a plurality of servers hosting plurality of communication tools, the communication data associated with a plurality of conversations involving one or more users;
    converting, by the computer, the communication data into a common format;
    generating, by the computer, a graph based upon the communication data in the common format based upon one or more characteristics identified in the communication data and the one or more users involved with the plurality of conversations;
    clustering, by the computer, the communication data in the graph according to the one or more characteristics and the one or more users, thereby generating one or more clusters around at least one of a characteristic and a user;
    generating user data for each of the one or more users based on the one or more clusters;
    generating project data for one or more projects based on the one or more clusters; and
    determining, by the computer, the set of one or more identified characteristics correlated with high performing projects, based on the user data and the project data, the one or more characteristics associated with the user data or project data.
10. The method according to embodiment 9, wherein the one or more identified characteristics include one or more selected from: communication tools, users associated with a conversation, users actively participating in the conversation, time of day associated with the conversation; or a topic of the conversation.
11. The method according to any one of embodiments 9-10, further comprising identifying, by computer, one or more topics associated with the plurality of conversations, wherein the one or more topics relate to a technical aspect of a respective project, and wherein identifying the set of one or more characteristics is performed based on the one or more topics.
12. The method according to any one of embodiments 9-11, further comprising identifying, by the computer, one or more sub-groups associated with a project, wherein each sub-group comprises one or more users associated with the project and associated with a communication activity that relates to a particular topic, and wherein identifying the set of one or more characteristics is performed based on the one or more sub-groups.
13. The method according to any one of embodiments 9-12, further comprising, for each communication tool, identifying, by the computer, a set of one or more characteristics of communication patterns correlated with high performing projects based on the user data and the set of one or more identified characteristics.
14. The method according to any one of embodiments 9-13, further comprising identifying, by the computer, a set of users who establish and maintain inter-team communications according to one or more characteristics of each user.

15. The method according to any one of embodiments 9-14, further comprising identifying, by the computer, teams that form bottom-up in a project or across projects, and are not explicit in the organization.
16. The method according to any one of embodiments 9-15, further comprising identifying, by the computer, a set of users for a project based on the user data and the set of one or more identified characteristics.
17. The method according to any one of embodiments 15-16, further comprising updating, by the computer, a data structure representing the team members corresponding to the project based on the set of one or more identified characteristics.
18. The method according to any one of embodiments 15-17, further comprising facilitating, by the computer, communication between a first user and a second user that were not previously in contact, based on the set of one or more identified characteristics.
19. The method according to any one of embodiments 9-18, further comprising causing display of a graphical user interface that includes the set of one or more identified characteristics.
20. The method according to any one of embodiments 9-19, further comprising:
   generating a notification based on the set of one or more identified characteristics; and
   causing the notification to be presented via a display.
21. The method according to any one of embodiments 9-20, further comprising identifying, by the computer, a characteristic of a conversation indicating a social interaction originated from a user.
22. The method according to any one of embodiments 9-21, further comprising identifying, by the computer, a characteristic of a conversation indicating a topical interaction originated from a user.
23. The method according to embodiment 22, further comprising identifying, by the computer, a topic in the topical interaction originated from the user.
24. The method according to any one of embodiments 9-23, further comprising identifying a project that lacks a characteristic identified in the set of one or more identified characteristics;
   identifying a user of the one or more users associated with the lacking identified characteristic; and
   recommending the user for the project.
25. The method according to any one of embodiments 9-24, further comprising determining, by the computer, a risk score indicative of a risk of failure of a project, based on the user data and the project data.
26. The method according to any one of embodiments 9-25, wherein the one or more communication activities corresponds to one or more of a conversation topic, a communication style, or a communication tool.
27. The method according to any one of embodiments 9-26, wherein identifying, by the computer, the set of one or more characteristics correlated with successful projects comprises:
   determining user scores for each user of the one or more users;
   determining project scores for each project of the one or more projects; and
   identifying one or more high performing projects based the project scores and the user scores.
28. The method according to embodiment 27, wherein at least one of the user score or project score is indicative of at least one selected from: relevancy of discussion topics, use of communication tools, timing of interactions, frequency of interactions, contributions to technical conversations, or socially relevant communications.
29. The method according to any one of embodiments 27-28, wherein identifying one or more high performing projects comprises comparing, by the computer, a project score associated with a particular project to a threshold.
30. The method according any one of embodiments 9-29, further comprising:
   receiving data indicating an assessment of a performance level associated with a project included in a training data set;
   generating a label for communication data associated with the project with the performance level assessment; and
   training a machine learning model based on the labeled data,
   wherein determining the set of one or more identified characteristics correlated with high performing projects is based at least in part on the model.
31. A system for determining a set of one or more identified characteristics correlated with high performing projects, comprising:
   one or more processors;
   a memory; and
   one or more programs, wherein the one or more programs are stored in the memory and configured to be executed by the one or more processors, the one or more programs including instructions for:
      receiving, by the computer, communication data from a plurality of servers hosting plurality of communication tools, the communication data associated with a plurality of conversations involving one or more users;
      converting, by the computer, the communication data into a common format;
      generating, by the computer, a graph based upon the communication data in the common format based upon one or more characteristics identified in the communication data and the one or more users involved with the plurality of conversations;
      clustering, by the computer, the communication data in the graph according to the one or more characteristics and the one or more users, thereby generating one or more clusters around at least one of a characteristic and a user;
      generating user data for each of the one or more users based on the one or more clusters;
      generating project data for one or more projects based on the one or more clusters; and
      determining, by the computer, the set of one or more identified characteristics correlated with high performing projects, based on the user data and the project data, the one or more characteristics associated with the user data or project data.
32. A non-transitory computer-readable storage medium storing one or more programs, the one or more programs comprising instructions, which when executed by one or more processors of one or more electronic devices, cause the electronic devices to:
   receive, by the computer, communication data from a plurality of servers hosting plurality of communication tools, the communication data associated with a plurality of conversations involving one or more users;

convert, by the computer, the communication data into a common format;

generate, by the computer, a graph based upon the communication data in the common format based upon one or more characteristics identified in the communication data and the one or more users involved with the plurality of conversations;

cluster, by the computer, the communication data in the graph according to the one or more characteristics and the one or more users, thereby generating one or more clusters around at least one of a characteristic and a user;

generate user data for each of the one or more users based on the one or more clusters;

generate project data for one or more projects based on the one or more clusters; and determine, by the computer, the set of one or more identified characteristics correlated with high performing projects, based on the user data and the project data, the one or more characteristics associated with the user data or project data.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

What is claimed is:

1. A computer-implemented method, the method comprising:

receiving, by a computer, first communication data from a plurality of servers hosting a plurality of communication tools, the first communication data associated with a plurality of conversations involving one or more users;

executing, by the computer, a plurality of conversion modules to convert the first communication data into a common format, wherein each of the plurality of conversion modules are respectively configured to convert data associated with a communication tool of the plurality of communication tools;

generating, by the computer, a graph based upon the first communication data in the common format based upon one or more characteristics identified in the first communication data and the one or more users involved with the plurality of conversations;

clustering, by the computer, the first communication data in the graph according to the one or more characteristics and the one or more users, thereby generating one or more clusters around at least one of a characteristic and a user;

generating user data for each of the one or more users based on the one or more clusters;

generating project data for one or more projects based on the one or more clusters; and determining, by the computer, a first set of one or more identified characteristics correlated with high performing projects, based on the user data and the project data, the one or more characteristics associated with the user data or the project data;

creating a message thread between a first user and a second user, based on the first set of one or more identified characteristics;

after creating the message thread, receiving, by the computer, second communication data from the first user and the second user based on at least one conversation between the first user and the second user using the message thread;

converting the second communication data into the common format using at least one of the plurality of conversion modules;

updating, by the computer, the graph to represent the first user, the second user, and the second communication data; and determining, based on the updated graph, a second set of one or more identified characteristics correlated with high performing projects.

2. The method according to claim 1, wherein the first set of one or more identified characteristics include one or more selected from: communication tools, users associated with a conversation, users actively participating in the conversation, time of day associated with the conversation; or a topic of the conversation.

3. The method according to claim 1, further comprising identifying, by computer, one or more topics associated with the plurality of conversations, wherein the one or more topics relate to a technical aspect of a respective project, and wherein determining the first set of one or more identified characteristics is performed based on the one or more topics.

4. The method according to claim 3, further comprising identifying, by the computer, one or more sub-groups associated with a project, wherein each sub-group comprises one or more users associated with the project and associated with a communication activity that relates to a particular topic, and wherein determining the first set of one or more identified characteristics is performed based on the one or more sub-groups.

5. The method according to claim 1, further comprising, for each communication tool, identifying, by the computer, a set of one or more characteristics of communication patterns correlated with high performing projects based on the user data and the first set of one or more identified characteristics.

6. The method according to claim 1, further comprising identifying, by the computer, a set of users who establish and maintain inter-team communications according to one or more characteristics of each user.

7. The method according to claim 1, further comprising identifying, by the computer, teams that form bottom-up in a project or across projects, and are not explicit in an organization.

8. The method according to claim 1, further comprising identifying, by the computer, a set of users for a project based on the user data and the first set of one or more identified characteristics.

9. The method according to claim 1, further comprising causing display of a graphical user interface that includes the first set of one or more identified characteristics.

10. The method according to claim 1, further comprising:
generating a notification based on the first set of one or more identified characteristics; and
causing the notification to be presented via a display.

11. The method according to claim 1, further comprising identifying, by the computer, a characteristic of a conversation indicating a social interaction originated from a user.

12. The method according to claim 1, further comprising identifying, by the computer, a characteristic of a conversation indicating a topical interaction originated from a user.

13. The method according to claim 12, further comprising identifying, by the computer, a topic in the topical interaction originated from the user.

14. The method according to claim 1, further comprising identifying a project that lacks a characteristic identified in the set of one or more identified characteristics;
identifying a user of the one or more users associated with the lacking identified characteristic; and
recommending the user for the project.

15. The method according to claim 1, further comprising determining, by the computer, a risk score indicative of a risk of failure of a project, based on the user data and the project data.

16. The method according to claim 1, wherein one or more communication activities correspond to one or more of a conversation topic, a communication style, or a communication tool.

17. The method according to claim 1, wherein determining, by the computer, the first set of one or more identified characteristics correlated with high performing projects comprises:
determining user scores for each user of the one or more users;
determining project scores for each project of the one or more projects; and
identifying one or more high performing projects based the project scores and the user scores.

18. The method according to claim 17, wherein at least one of the user scores or the project scores are indicative of at least one selected from: relevancy of discussion topics, use of communication tools, timing of interactions, frequency of interactions, contributions to technical conversations, or socially relevant communications.

19. The method according to claim 17, wherein identifying the one or more high performing projects comprises comparing, by the computer, a project score associated with a particular project to a threshold.

20. The method according to claim 1, further comprising:
receiving data indicating an assessment of a performance level associated with a project included in a training data set;
generating a label for communication data associated with the project with the assessment of the performance level; and
training a machine learning model based on the label for the communication data associated with the project,
wherein determining the set of one or more identified characteristics correlated with high performing projects is based at least in part on the model.

21. A system comprising:
one or more processors;
a memory; and
one or more programs, wherein the one or more programs are stored in the memory and configured to be executed by the one or more processors, the one or more programs including instructions for:
receiving, by a computer, first communication data from a plurality of servers hosting a plurality of communication tools, the first communication data associated with a plurality of conversations involving one or more users;
executing, by the computer, a plurality of conversion modules to convert the first communication data into a common format, wherein each of the plurality of conversion modules are respectively configured to convert data associated with a communication tool of the plurality of communication tools;
generating, by the computer, a graph based upon the first communication data in the common format based upon one or more characteristics identified in the first communication data and the one or more users involved with the plurality of conversations;
clustering, by the computer, the first communication data in the graph according to the one or more characteristics and the one or more users, thereby generating one or more clusters around at least one of a characteristic and a user;
generating user data for each of the one or more users based on the one or more clusters;
generating project data for one or more projects based on the one or more clusters; and
determining, by the computer, a first set of one or more identified characteristics correlated with high performing projects, based on the user data and the project data, the one or more characteristics associated with the user data or the project data;
creating a message thread between a first user and a second user, based on the first set of one or more identified characteristics;
after creating the message thread, receiving, by the computer, second communication data from the first user and the second user based on at least one conversation between the first user and the second user using the message thread;
converting the second communication data into the common format using at least one of the plurality of conversion modules;
updating, by the computer, the graph to represent the first user, the second user, and the second communication data; and
determining, based on the updated graph, a second set of one or more identified characteristics correlated with high performing projects.

22. A non-transitory computer-readable storage medium storing one or more programs, the one or more programs comprising instructions, which when executed by one or more processors of one or more electronic devices, cause the electronic devices to:
receive, by a computer, first communication data from a plurality of servers hosting a plurality of communication tools, the first communication data associated with a plurality of conversations involving one or more users;
execute, by the computer, a plurality of conversion modules to convert the first communication data into a common format, wherein each of the plurality of conversion modules are respectively configured to convert data associated with a communication tool of the plurality of communication tools;
generate, by the computer, a graph based upon the first communication data in the common format based upon one or more characteristics identified in the first communication data and the one or more users involved with the plurality of conversations;

cluster, by the computer, the first communication data in the graph according to the one or more characteristics and the one or more users, thereby generating one or more clusters around at least one of a characteristic and a user;

generate user data for each of the one or more users based on the one or more clusters;

generate project data for one or more projects based on the one or more clusters; and determine, by the computer, a first set of one or more identified characteristics correlated with high performing projects, based on the user data and the project data, the one or more characteristics associated with the user data or the project data;

create a message thread between a first user and a second user, based on the first set of one or more identified characteristics;

after creating the message thread, receive, by the computer, second communication data from the first user and the second user based on at least one conversation between the first user and the second user using the message thread;

convert the second communication data into the common format using at least one of the plurality of conversion modules;

update, by the computer, the graph to represent the first user, the second user, and the second communication data; and determine, based on the updated graph, a second set of one or more identified characteristics correlated with high performing projects.

* * * * *